(12) United States Patent
Badami

(10) Patent No.: US 11,390,849 B2
(45) Date of Patent: Jul. 19, 2022

(54) NK-MEDIATED IMMUNOTHERAPY AND USES THEREOF

(71) Applicants: FONDAZIONE RI.MED, Palermo (IT); ISTITUTO MEDITERRANEO PER I TRAPIANTI E TERAPIE AD ALTA SPECIALIZZAZIONE . ISMETT, Palermo (IT)

(72) Inventor: Ester Badami, Palermo (IT)

(73) Assignees: FONDAZIONE RI.MED, Palermo (IT); ISTITUTO MEDITERRANEO PER I TRAPIANTI E TERAPIE AD ALTA SPECIALIZZAZIONE . ISMETT, Palermo (IT)

( * ) Notice: Subject to any disclaimer, the term of this patent is extended or adjusted under 35 U.S.C. 154(b) by 446 days.

(21) Appl. No.: 16/464,823

(22) PCT Filed: Nov. 29, 2017

(86) PCT No.: PCT/EP2017/080848
§ 371 (c)(1),
(2) Date: May 29, 2019

(87) PCT Pub. No.: WO2018/099988
PCT Pub. Date: Jun. 7, 2018

(65) Prior Publication Data
US 2019/0322985 A1 Oct. 24, 2019

(30) Foreign Application Priority Data
Nov. 29, 2016 (IT) .................. 102016000121081

(51) Int. Cl.
*C12N 5/0783* (2010.01)
*A61P 35/00* (2006.01)
*A61K 35/17* (2015.01)
*A61K 45/06* (2006.01)

(52) U.S. Cl.
CPC ............ *C12N 5/0646* (2013.01); *A61K 35/17* (2013.01); *A61K 45/06* (2013.01); *A61P 35/00* (2018.01); *C12N 2501/2302* (2013.01); *C12N 2501/2315* (2013.01); *C12N 2501/24* (2013.01)

(58) Field of Classification Search
CPC .......... C12N 5/0646; C12N 2501/2302; C12N 2501/2315; C12N 2501/24; A61K 35/17
See application file for complete search history.

(56) References Cited

U.S. PATENT DOCUMENTS

2015/0010583 A1* 1/2015 Spanholtz ........ A61K 39/39558
424/174.1

FOREIGN PATENT DOCUMENTS

| WO | 2012/089736 A1 | 7/2012 |
| WO | 2016/020434 A1 | 2/2016 |

OTHER PUBLICATIONS

Smyth et al., J Exp Med (2001) 193 (6): 661-670 (Year: 2001).*
Ohira et al., Transplantation. Dec. 27, 2006;82(12):1712-9 (Year: 2006).*
Ohira et al., J Clin Invest . . . 2009;119:3226-3235 (Year: 2009).*
Konjevic; et al., "Natural killer cell receptors: alterations and therapeutic targeting in malignancies", Immunologic Research, Humana Press, Inc., vol. 64, No. 1, 2015, pp. 25-35.
Harmon; et al., "Tissue-resident Eomes(hi) T-bet(lo) CD56(bright) NK cells with reduced proinflammatory potential are enriched in the adult human liver", European Journal of Immunology, vol. 46, No. 9, 2016, pp. 2111-2120.
ISA/EP, PCT International Search Report and Written Opinion, dated Feb. 7, 2018, which were issued in connection with corresponding PCT Application No. PCT/EP2017/080848 (10 pages).

* cited by examiner

*Primary Examiner* — Daniel C Gamett
(74) *Attorney, Agent, or Firm* — Lucas & Mercanti, LLP

(57) ABSTRACT

The present invention refers to a method for the production of activated CD3-CD56+ NK cells, activated CD3-CD56 NK+ cells obtainable with the method, their use, in particular for the treatment of a tumor, preferably a hepatocellular carcinoma (HCC), for use in the treatment and/or prevention of an HCV infection, for use in the treatment and/or prevention of a post-liver transplant HCV reinfection, or for use for prevention of a post-liver transplant HCC recurrence. The invention also concerns pharmaceutical compositions including the activated CD3-CD56+ NK cells.

7 Claims, 11 Drawing Sheets

*Adapted from: Garcia-Retortillo Hepatology 2002, 35:3 680-687 [6].*

*Adapted from: Ohira M et al JCI 2009, 119:11 3226-3235 [11].*

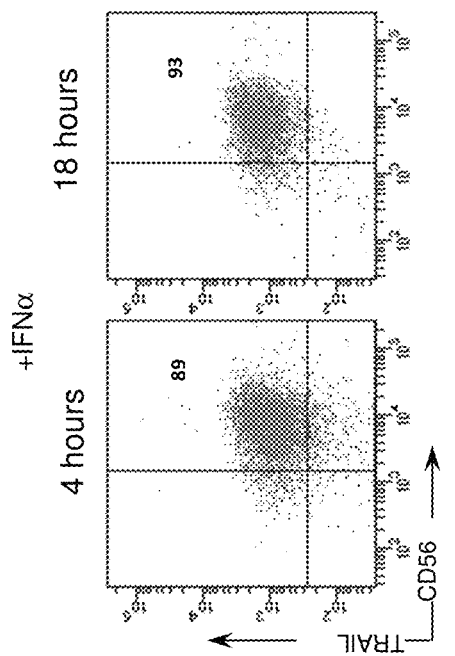
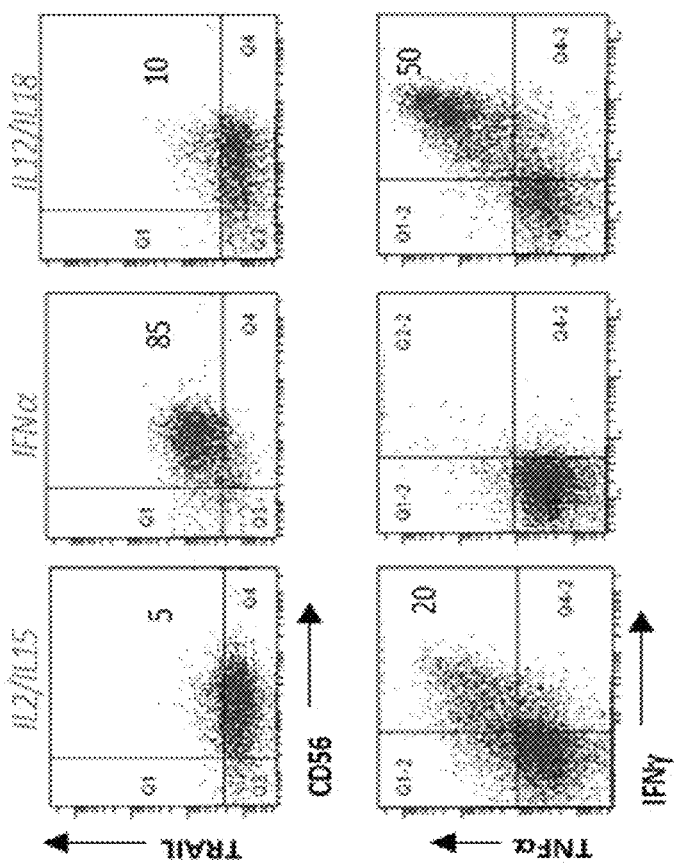
Figure 4b
Figure 4a

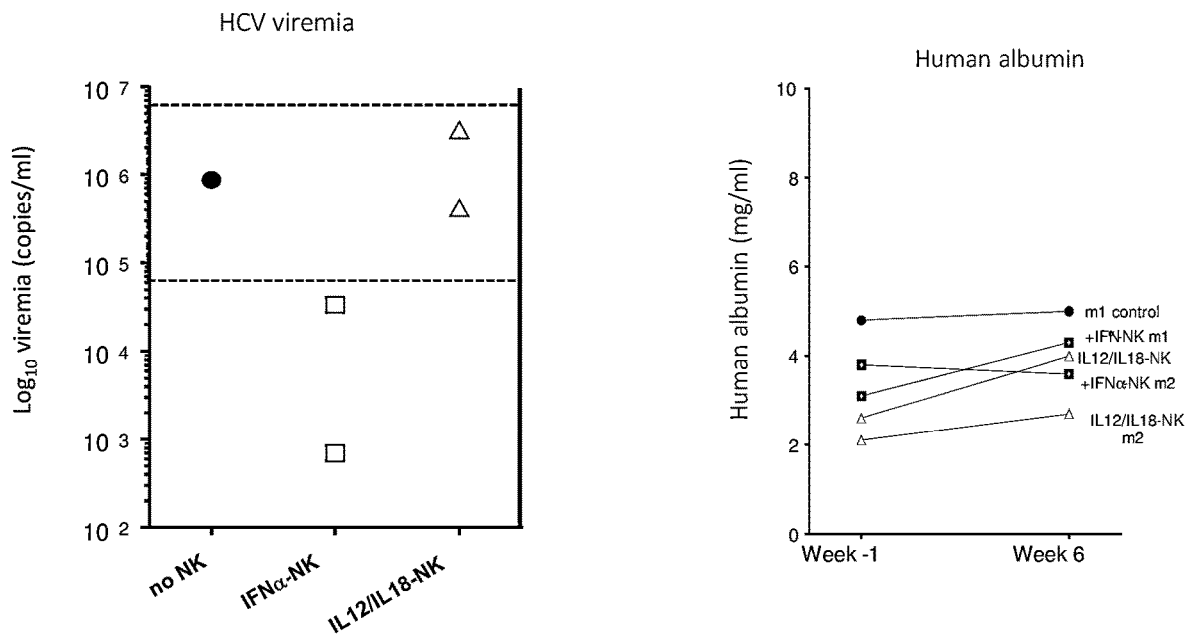
Figure 5e
Figure 5f
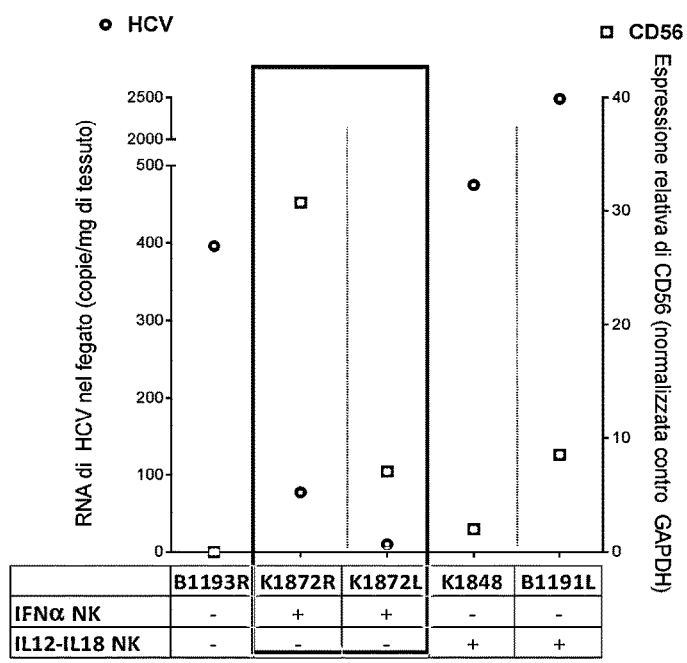
Figure 5g

NK-MEDIATED IMMUNOTHERAPY AND USES THEREOF

CROSS-REFERENCE TO RELATED APPLICATIONS

This application is a 371 of PCT/EP2017/080848, filed Nov. 29, 2017, which claims the benefit of Italian Patent Application No. 102016000121081, filed Nov. 29, 2016.

TECHNICAL FIELD

The present invention refers to a method for the production of activated $CD3^-CD56^+$ NK cells, activated $CD3^-CD56\ NK^+$ cells obtainable with said method, use thereof, in particular for the treatment of tumor, preferably a hepatocellular carcinoma (HCC), for the treatment and/or prevention of an HCV infection, for the treatment and/or prevention of post-liver transplant HCV reinfection, or for the prevention of post-liver transplant hepatocellular carcinoma recurrence. The invention also concerns pharmaceutical compositions comprising said activated $CD3^-CD56^+$ NK cells.

BACKGROUND OF THE INVENTION

HCC and HCV

Hepatocellular carcinoma (HCC) is currently the fifth most common malignancy and the second cause of mortality in male adult cancer population [1]. In approximately 80% of the cases, HCC is associated with an hepatitis C (HCV) chronic infection [1]. HCV mainly infects human hepatocytes, leading to a chronic liver infection that causes cirrhosis, liver decompensation, hepatocellular carcinoma, and liver dysfunction. HCV causes chronic infection in 60-80% of patients as the virus evades immune defenses impairing the function of the cells involved in the innate and adaptive immune response [2]. To date, an anti-HCV vaccine is not available. Current hepatitis C treatments are made up of combinations of drugs called direct-acting antivirals (DAAs). DAAs directly target the hep C virus in different ways to stop it from making copies of itself. There are four classes of DAAs:
1) NS3/4A Protease Inhibitors (PIs); work by blocking a viral enzyme (protease) that enables the hep C virus to survive and replicate in host cells.
2) Nucleoside and Nucleotide NS5B Polymerase Inhibitors; They directly target the hep C virus to stop it from making copies of itself in the liver. They attach themselves onto the genetic information, called RNA, to block the virus from multiplying;
3) NS5A Inhibitors; They block a virus protein, NS5A, that HCV needs to reproduce and for various stages of infection.
4) Non-Nucleoside NS5B Polymerase Inhibitors; They work to stop HCV from reproducing by inserting themselves into the virus so that other pieces of the hep C virus cannot attach to it. However, there is currently no information on the side effects of long-term treatment such as, for example, the onset of drug resistance-associated substitutions (RASs) [3], the effects on liver tumor in HCC patients with associated HCV infection [4] or extrahepatic side effects. Finally, the costs of the treatment are still extremely high, and therefore not affordable by all categories of infected patients. HCC and HCV are indications to liver transplant. However, the recurrence of post-transplant HCV occurs in almost all recipients who are not treated pharmacologically, whereas HCC recurrence occurs in 10-60% of patients 1-2 years after the transplant [5].

Some studies demonstrated that the incidence of post-transplant HCV recurrence is correlated with pre-transplant viremia values. In other words, the higher the pre-transplant viremia, the more aggressive will be the post-transplant reinfection. Similarly, the possibility of no post-transplant recurrence increases in an environment with low-viremia values before the transplant [6, 7]. The kinetic of HCV liver reinfection during transplant was studied in detail and shows a dramatic drop in peripheral viremia values immediately after the infected organ removal, which lasts for the first 16-24 hours post-transplant [8]. At later time points, viremia critically increases to values significantly exceeding those observed pre-transplant. This is partly due to the immunosuppressive regimen administered to recipients, and partly because the virus colonizes a new healthy organ with no scar and/or fibrotic areas (FIG. 1). In the light of these studies, it can be concluded that there is a 16-24-hour time-window with almost no viremia, during which adjuvant therapies could be used to enhance the probability of successful viral eradication.

Also in the case of HCC, timely treatment upon liver removal could improve the prevention of post-transplant short- and long-term HCC recurrence.

NK Cells

Natural Killer (NK) cells are key players in the initial response to cancer and viral infections. In the presence of target cells, NK cells respond releasing inflammatory cytokines (IFNγ, TNFα, GM-CSF, etc.) or Granzyme A/B and Perforin, negatively interfering with the vitality of target cells or with the viral cycle. Alternatively, NK cells kill the target cell by cell-to-cell interactions, with an overexpression of membrane receptors such as TRAIL (TNF-related Apoptosis-Inducing Ligand) and FASL (Fas Ligand) [9]. NK cells express specific membrane receptors for MHC-I (Major Histocompatibility Complex Class I), molecules physiologically expressed by all cells and that allow cells from the same organism (self) to be recognized, thus avoiding self-destruction processes. Receptors expressed by NK cells may be inhibitors, such as some types of KIR (Killer-cell Immunoglobulin-like Receptor) that recognize MHC-I molecules. NK cells can also express activating receptors such as NKG2D, NKp30, NKp44, NKp46, and CD16, which recognize ligands aberrantly expressed by tumor and/or infected cells. NK cells can recognize tumor or infected target cells as these express an altered phenotype. For example, an infected cell can express high levels of a ligand for activating receptors expressed by NK cells, or express fewer ligands for receptors sending inhibitory signals. When the activating signals prevail over the inhibitory signals, NK cells activate and kill the target cells both releasing soluble factors and inducing cell death by apoptosis.

For dozens of years NK cells have been used in anti-tumor adoptive immunotherapy both in auto- and allo-transplantation [10]. The possibility of using NK cells to prevent post-transplant HCC and HCV recurrence is currently under study.

The underlying hypothesis of the present invention is that the infusion of NK cells isolated from an healthy donor of a liver transplant recipient, at the time of the transplant, can boost his/her immune system, such system being compromised by the anti-rejection therapy administered during organ transplant. Moreover, it is known that patients with chronic HCV infection and/or liver tumor have an impaired immune system [11]. Therefore, restoring recipient's immune defenses with healthy donor's NK cells becomes therapeutically relevant.

During donor's liver removal, in order to ensure tissue integrity, the graft is necessarily perfused with an enriched solution such as Celsior solution, adjuvated with ACD (Acid-Citrate-Dextrose) anticoagulant to prevent the formation of clots. NK cells are particularly enriched in liver perfusate where they represent 30-50% of mononuclear cells (FIG. 2) [12].

NK cells are ideal cells for immunotherapy in order to target prevention of post-transplant HCC and/or HCV recurrence, for several reasons. Firstly, NK cells are not subject to functional suppression induced by post-transplant suppressive immunotherapy, which is, instead, specific for lymphocytes T. Secondly, a large number of vital and functional NK cells can be isolated from liver perfusate at the time of liver transplant. Then a large number of cells may be infused within the first 16-24 hours after the transplant. Timing can be crucial to enhance the chances of a successful therapy. NK cells are usually isolated from the peripheral blood where a significantly lower number of cells can be isolated. In fact, NK cells in the blood represent only 5-15% of mononuclear cells. Further, volumes of collected blood are considerably lower compared to volumes of donor's liver perfusate. In a clinical study conducted by a team in Miami, NK cells isolated from a donor's liver perfusate were used to treat post-transplant HCC recurrence (NCT01147380). In this study, the cells (Safety Study of Liver Natural Killer Cell Therapy for Hepatoma Liver Transplantation (MIAMINK) NCT01147380) are only activated with IL2, and inoculated in the recipient several days after the transplant [13, 14].

SUMMARY OF THE INVENTION

In the present invention it was found that NK cell function can be directed towards a more efficient antiviral and anti-tumor phenotype. The specific combination of cytokines [IL2+IL15] and [IFNα] activates NK cells very efficiently, providing said activated NK cells superior anti-HCV and anti-HCC activity, when compared to activation with the cytokine cocktail [IL2+IL15] and [IL12+IL18] or with the single combination of [IL2+IL15]. Further the cell extraction protocol of the present invention is advantageous when compared to other procedures used in NK-mediated therapy clinical trials known to date. NK cells are not isolated from peripheral blood but from liver perfusate, from which a considerably higher number of cells can be obtained. This is not only because liver perfusate cab be obtained in much larger quantities (0.5-1.5 liters compared to ml obtainable from peripheral blood, even by leukapheresis), but also because NK cells are highly present in the liver compared to other organs (30-50% in the liver compared to 5-15% in the peripheral blood) [12]. In addition large number of NK cells may be obtained when proceeding to liver transplant. The possibility of isolating large numbers of NK cells at the time of the liver transplant is a unique clinical and therapeutic advantage because a timely treatment could actually make a difference in the prevention of post-transplant HCV and HCC recurrence. Furthermore, NK cells come from the liver of the donor, not from a third donor, thus reducing the possibilities of a potential rejection and increasing NK cell function that migrate in the liver—the target organ—finding an autologous micro-environment.

The present invention therefore provides a method for the production of activated CD3$^-$CD56$^+$ NK cells comprising the steps of:
a) isolating CD3$^-$CD56$^+$ NK cells from a liver perfusate;
b) cultivating said isolated CD3$^-$CD56$^+$ NK cells in the presence of IL-2, IL-15 and IFNα

Preferably, the method further comprises expanding the isolated CD3$^-$CD56$^+$ NK cells.

Preferably, said isolated CD3$^-$CD56$^+$ NK cells are expanded in the presence of irradiated cells, preferably autologous cells. More preferably, said isolated CD3$^-$CD56$^+$ NK cells are expanded for from approximately or about 8 hours to approximately or about 168 hours in the presence of IL-2 and IL-15.

Preferably, the amount of IL-2 is between 100-1000 IU/ml, preferably between 200-1000 IU/ml, the amount of IL-15 is between 20-50 ng/ml, and the amount of IFNα is between 10-1000 ng/ml.

In a preferred embodiment, said isolated CD3$^-$CD56$^+$ NK cells are cultivated with IFNα for from approximately or about 4 hours to approximately or about 24 hours.

It is a further object of the invention activated CD3$^-$CD56$^+$ NK cells obtainable by the method of the present invention wherein said activated CD3$^-$CD56$^+$ NK cells express at the surface the TRAIL molecule.

Preferably, said activated CD3$^-$CD56$^+$ NK cells are for use for the treatment and/or prevention of a tumor. Preferably, the tumor is a HCC.

Preferably, said activated CD3-CD56$^+$ NK cells are used for the treatment and/or prevention of HCV infection.

Preferably, said activated CD3-CD56$^+$ NK cells are used for the treatment and/or prevention of a HCV re-infection after liver graft, or for use in the prevention of a post-transplant HCC recurrence.

In a preferred embodiment, said activated CD3-CD56$^+$ NK cells are administered between from approximately 8 hours to approximately 12 hours, preferably between approximately 16 hours and approximately 48 hours after the liver transplant, preferably between approximately 24 hours and approximately 48 hours after the liver transplant. Preferably, said cells are injected in the liver and/or intravenously.

It is a further object of the invention a pharmaceutical composition comprising the activated CD3$^-$CD56$^+$ NK cells and pharmaceutically acceptable excipients.

Preferably, the pharmaceutical composition additionally includes a further therapeutic agent, preferably an anti-viral and/or an anti-tumor agent and/or an immune checkpoint modulator agent.

Preferably, the further therapeutic agent is an antitumor drug. In particular, this drug is a Receptor Tyrosine Kinase Inhibitor (RTKI), more preferably, this inhibitor is Sorafenib.

Preferably, the therapeutic agent is a monoclonal antibody that modulates the immune checkpoints. In particular, this antibody is a specific blocking antibody for the CTLA-4 protein receptor. More preferably, this blocking antibody is tremelimumab and/or ipilimumab.

Preferably, the therapeutic agent is a monoclonal antibody that modulates the immune checkpoints. In particular, this antibody is a specific blocking antibody for the PD-1 protein receptor. More preferably, this blocking antibody is pidilizumab and/or nivolumab and/or pembrolizumab.

More preferably, the CTLA-4 blocking antibodies can be used in combination with PD-1 receptor antibodies [15].

Preferably, the therapeutic agent is an antiviral agent, preferably an anti-HCV agent. In particular, the selected agent belongs to the latest generation direct-acting antiviral (DAA) drugs, according to national and international guidelines (e.g. EASL for Europe; AASLD for the United States). This agent can be selected from a group composed of: a protease inhibitor, a nucleoside and/or nucleotide inhibitor, a polymerase inhibitor, a NS3/4A inhibitor, a NS5A inhibitor, a NS5B inhibitor, a kinase inhibitor, or a combination of the above.

NS3/4A protease inhibitors are inhibitors of the NS3/4A serine protease, an enzyme involved in post-translational processing and replication of HCV. Protease inhibitors disrupt HCV by blocking the NS3 catalytic site or the NS3/NS4A interaction [16]

Nucleoside and/or nucleotide inhibitors are activated within the hepatocyte through phosphorylation to nucleoside triphosphate, which competes with nucleotides, resulting in chain termination during RNA replication of the viral genome. As a class, nucleoside polymerase inhibitors (NPIs) have moderate to high efficacy across all six genotypes, with equal efficacy among subtypes 1a and 1b and have a very high barrier to resistance Regarding the Polymerase inhibitors, the four allosteric sites that act as targets for non-nucleoside polymerase inhibitors (NNPIs) are thumb domains 1 and 2 and palm domains 1 and 2. As a class, NNPIs are less potent, are more genotype specific (all NNPIs in clinical development have been optimized for genotype 1), have a low to moderate barrier to resistance, and have variable toxicity profiles [17]. Consequently, this class of drug has been studied primarily as an adjunct to more potent compounds with higher barriers to resistance.

Regarding the NS5A inhibitor, the NS5A protein plays a role in both viral replication and the assembly of the hepatitis C virus (HCV) [18, 19]. However, the precise molecular mechanisms by which NS5A accomplishes these functions are uncertain. Thus, the exact mechanism of action of HCV NS5A inhibitors is unclear.

Regarding NS5B inhibitor, NS5B is an RNA-dependent RNA polymerase involved in post-translational processing that is necessary for replication of HCV. The enzyme has a catalytic site for nucleoside binding and at least four other sites at which a non-nucleoside compound can bind and cause allosteric alteration. The enzyme's structure is highly conserved across all HCV genotypes, giving agents that inhibit NS5B efficacy against all six genotypes [16].

Kinase inhibitors includes Sorafenib which is a small inhibitor of several tyrosine protein kinases, such as VEGFR, PDGFR and Raf family kinases [20]. Sorafenib treatment induces autophagy which may suppress tumor growth [21]. However, autophagy can also cause drug resistance [22].

For information on DAAs see https://www.uptodate.com/contents/direct-acting-antivirals-for-the-treatment-of-hepatitis-c-virus-infection.

More preferably, the protease inhibitor is simeprevir, glecaprevir, grazoprevir, paripratevir, the polymerase inhibitor is sofosbuvir, the NS3/4A inhibitor is Asunaprevir, the NS5A inhibitors are Ombitasvir, Daclatasvir and/or Ledipasvir, Elbasvir, Pibrentasvir, the NS5B inhibitor is Velpatasvir Dasabuvir, and the kinase inhibitor is Sorafenib. Preferably, the agent is selected from a group composed of: paritaprevir, ritonavir, dasabuvir, grazoprevir, elbasvir, and ribavirin. Isolated $CD3^-CD56^+$ NK cells can be expanded, particularly by means of feeder cells. Feeder cells are lethally irradiated. The irradiation prevents their replication so that only NK cells can expand. Examples of feeder cells include K562 or peripheral blood mononuclear cells (PBMCs), particularly autologous. Autologous PBMCs are cells deriving from the donor's liver perfusate. The feeder cells and the IL2 and IL15 growth factors are preferably added on day 1 (when the NK cells are isolated from the perfusate). The culture medium is preferably changed with fresh medium+IL2/IL15, preferably every 2-3 days.

IFNα is preferably added approximately or about 8 hours before the experiment or the infusion in the patient, preferably approximately or about 12 hours before the experiment or the infusion in the patient, still preferably about 18 hours before the experiment or the infusion in the patient. Times may vary according to the amount of collected cells. The skilled person in the art can easily determine the appropriate time.

Preferably, the isolated $CD3^-CD56^+$ NK cells can be initially activated with irradiated feeders+IL2 and IL15, preferably for approximately 5-6 days. Schematically, the protocol preferably includes the following steps:

Day 1) Feeders+IL2/IL15+IFNα for 8-18 hours. Infusion in the patient with a fraction of NK cells.

Expand the remaining fraction of NK cells for a second injection.

Day 2/3) Change of medium+IL2/IL15

Day 5/6) addition of IFNα overnight

Day 6/7) Experiment/patient inoculation

Particularly, in the present invention, activated $CD3^-CD56^+$ NK cells represent a NK cell population in which less than 1% of $CD3^+$ cells is present. Cells are called activated because they express in particular the TRAIL marker. NK cells are activated and eliminate target cells (tumor cells or infected cells) either by releasing soluble factors (Granzyme A/B, Perforin, Interferon gamma, TNF-alpha, etc.) or by contact with the target cell by means of TRAIL and FASL surface proteins, thereby causing apoptotic cell death.

In the present invention, liver perfusate is the fluid obtained from graft/organ perfusion with Celsior solution, an enriched solution that is specific for organ preservation. Therefore, the donor's blood is mixed with Celsior. In the case of liver, the hepatic aorta is clamped and the Celsior solution is injected through the portal vein and hepatic artery. The blood mixed with Celsior solution is drained from donor's suprahepatic inferior vena cava, just after donor's caval venting (approx. 5 liters). Later, upon implanting the liver in the recipient, the liver is perfused on the operation table with an additional liter of Celsior solution.

In the present invention an HCC is a malignant primary liver cancer.

BRIEF DESCRIPTION OF THE DRAWINGS

The present invention will be described by means of non-limiting examples, with reference to the following figures.

In the following figures, the group "IL-2/IL-15" means that NK cells are activated with a mixture of IL-2 and IL-15, the group "IFNα" means that NK cells are activated with a mixture of IL-2 and IL-15 and IFNα, the group "IL12/IL18" means that NK cells are activated with a mixture of IL-2 and IL-15 and a mixture of IL-12 and IL-18, as further detailed in the method section.

DETAILED DESCRIPTION OF THE INVENTION

Figure 1:
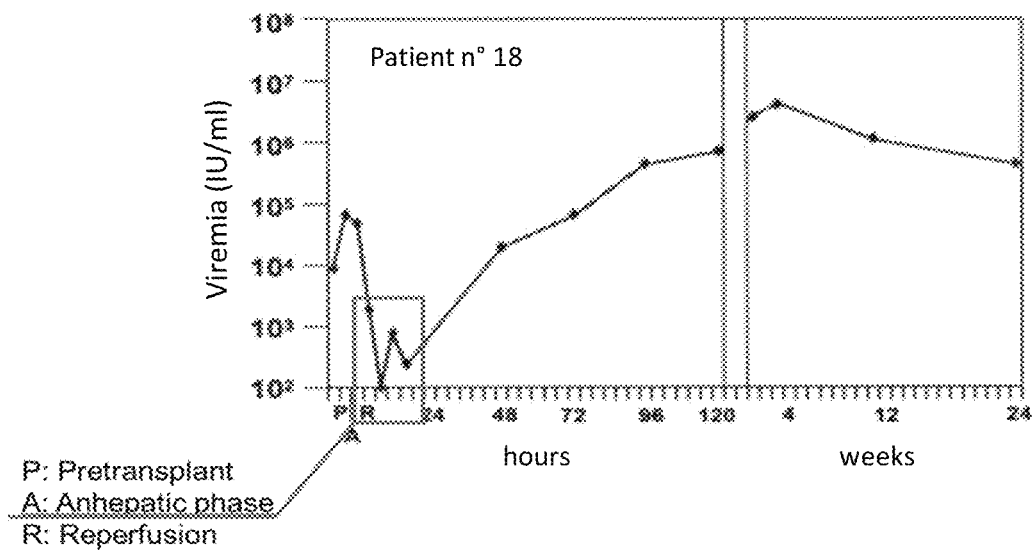
FIG. 1: Kinetics of HCV infection before (P: Pre-transplant), during (A: Anhepatic phase), and after (R: Reperfusion) liver transplant (adapted from [8]).
Figure 2:
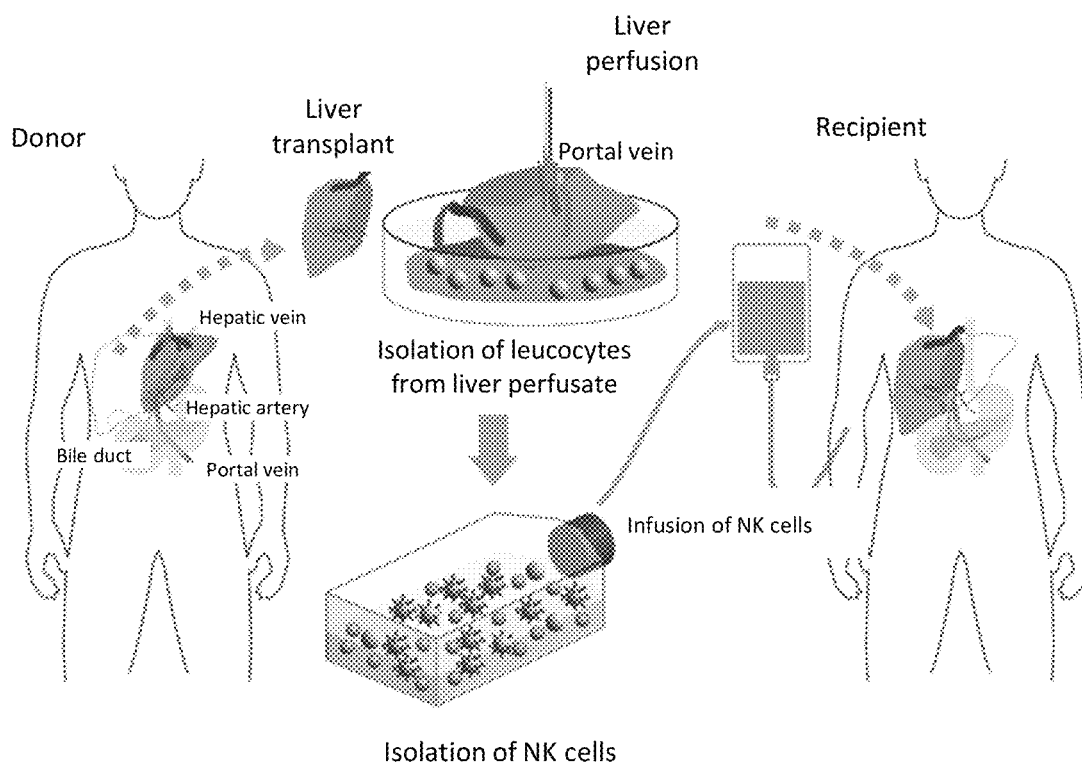
FIG. 2: Strategy for NK-mediated cell therapy. Donor's liver is perfused at the time of removal and the perfusate is used as a tissue from which to obtain large numbers of NK cells. Cells are briefly activated in vitro and promptly infused in the recipient in the immediate post-transplant phases (adapted from [13]).

Materials and Methods
Liver Perfusate.

When the graft is removed from the donor, the aorta is clamped and the liver perfused in situ through the portal vein and the hepatic artery, with approximately 5 liters of Celsior (Glutathione 3 mmol; Mannitol 60 mmol; Lactobionic acid 80 mmol; Glutamic acid 20 mmol; Sodium hydroxide 100 mmol; Calcium chloride, 2H20 0.25 mmol; Potassium chloride 15 mmol; Magnesium chloride, 6H20 13 mmol, Histidine 30 mmol, Water for injections up to 1 litre) (Genzyme) to remove the blood from the vasculature. The liver perfusate is collected by aspiration in an Autotransfusion Reservoir (ATR40; Fresenius-Kabi) using the vacuum system present in the operating room where the removal is conducted, by means of a sterile suction tubing system, connected to a sterile drainage system consisting of a suction tube with a pool suction cannula, to be handed to the surgeon to aspirate the perfusate. Before aspirating the perfusate, the reservoir must be filled with anticoagulant (Acid-Citrate-Dextrose, ACD, B223011, Fresenius-Kabi). The recommended amount is 250 ml for each reservoir. The reservoir can therefore be presumed to contain up to 2750 ml of liver perfusate and 250 ml of ACD (10%). Perfusate collection must be performed in such a way to ensure perfusate sterility. Once full, the reservoirs are closed with appropriate sterile caps, which must be placed at the connections of the suction tubes with the sterile drainage. All caps are then blocked and secured with specific clamps. Following the resection the liver is placed in an isolation bag (Isolation Bag, Steri-Drape 1003, 3M) to be transported to the operating room in a thermal insulated container with ice to maintain a constant temperature (approximately 4° C.). Upon arrival to the operating room, the organ is reperfused with one additional liter of Celsior solution and sealed in the 3M Isolation Bag. From the moment the liver is reopened to be transplanted, the residual perfusate in the 3M Isolation Bag is suctioned using a further reservoir that requires no anticoagulant treatment. The reservoirs containing the perfusate are maintained at a constant temperature of approximately 4° C. until processing. The perfusate is filtered during the suctioning in the reservoir, equipped with a 40 μm filter.

The perfusate is transferred in 250 ml conical tubes and concentrated by centrifugation at 2,000 rpm, 10 minutes (acceleration 9, deceleration 7, temperature 20° C., Heraeus Multifuge 4KR). The pellet is again filtered with the 40 μm filter of a reservoir (ATR40, Fresenius-Kabi), and transferred in a BMSC double apheresis bag (9007341, Fresenius-Kabi). The buffy coat is obtained by apheresis using the Com.TEC (Fresenius-Kabi) platform. An isolation kit with a closed circuit of tubing and collection bags is used to isolate the leukocytes (P1Y, 9400421, Fresenius-Kabi) using the "bone marrow isolation" program available on the Com.TEC apheresis device. After centrifugation (2,000 rpm, 10 minutes 20° C.), the buffy coat is purified of the residual red cells using a solution containing ammonium chloride and potassium (cGMP ACK lysis solution, A1049201 Thermofisher Scientific). After centrifugation, the pellet is re-suspended in RPMI complete medium (BE12-167F, Lonza), 10% FBS (F7524, Sigma-Aldrich) penicillin/streptomycin antibiotics (P4333, Sigma-Aldrich) and L-glutamin (BE17-605E, Lonza), and filtered in a reservoir with a 40 μm filter to remove cellular aggregates. Platelets are removed with low-speed centrifugation (200×g, 10 minutes, 20° C.). The pellet is re-suspended in complete medium. The cell count and vitality are determined by exclusion assays with Trypan Blue coloring (17-942E, Lonza) and Burker chamber. Samples with a vitality above 90% are considered valid.

Flow Cytometry.

Cellular phenotype is characterized by flow cytometry using the FACSAria II dual-laser cytofluorimeter (BD Biosciences). Data are analyzed with FACSDiva 8.0.1 software. Briefly, $10^6$ cells are re-suspended in buffer containing PBS (D8537, Sigma-Aldrich), 2% FBS and 0.1% NaN3 (S2002, Sigma-Aldrich), and incubated with monoclonal antibodies conjugated with fluorochromes: CD3-FITC (130-080-401), CD45-APC (130-091-230), CD56-PE (130-090-755), CD16-FITC (130-091-244), CD16-APC (130-091-246), NKp44-PE (130-092-480) (Miltenyi Biotec); CD56-APC-eFluor-780 (47-0567), TRAIL-PE (12-9927), NKG2D-PerCP-eFluor710 (46-5878) (eBioscience); CD3-PerCP (340663), CD56-AlexaFluor-700 (557919) NKp30-AlexaFluor-647 (558408) NKp46-PE-Cy7 (562101) (BD Biosciences). For intracellular marking, cells are fixed and permed with the CytoFix/CytoPerm kit (554722, BD Pharmingen) following the manufacturer's instructions, and incubated with monoclonal antibodies IFNγ-PE-Cy7 (557643, BD Pharmingen) and TNFα-AlexaFluor-700 (56-7349, eBioscience) for 30 minutes at 4° C.

CD3$^-$CD56$^+$ Cell Isolation—Research-Grade Protocol.

The buffy coat obtained from the liver perfusate is processed for specific isolation of CD3$^-$CD56$^+$ NK cells using magnetic bead-conjugated monoclonal antibodies (Miltenyi Biotec). For in vitro preliminary experiments, research grade reagents are used (anti-human CD3 microbeads 130-050-101; anti-human CD56 microbeads 130-050-401 and QuadroMACS separators (130-090-976) with MACS Multi-Stand (130-042-303), and LS columns (130-042-401, Miltenyi Biotec) for manual separation, or AutoMACS Pro Separator (130-092-545) and AutoMACS columns (130-021-101) for automated separation. The buffy coat undergoes a double cycle separation: in the first cycle CD3$^+$ cells are eliminated (negative selection); in the second cycle CD56$^+$ cells are isolated (positive selection) following the manufacturer's instructions.

Activation and Expansion of NK Cells—Research-Grade Protocol.

NK cell vitality is determined by exclusion with Trypan Blue. CD3$^-$CD56$^+$ NK cells are expanded in vitro with K562 cells (code BS TCL 33, Istituto Sperimentale Zooetcnico della Lombardia ed Emilia Romagna, I.Z.S.L.E.R., Brescia, Italy) lethally irradiated (120Gy, RADGIL irradiator, serial no. 048785002, Gilardoni) (report NK:K562=20: 1) in the presence of rhu-IL2 (500-1000 U/ml, Proleukin, Novartis) and rhu-IL15 (20-50 ng/ml, 130-095-765, Miltenyi Biotec) in Stem Cell Growth Medium (SCGM, 20802, CellGRO), 5-10% FBS, Pen/Strep; L-Glu ("resting" NK, IL2/IL15 NK cells). Half of the medium is replaced every 2-3 days with fresh medium containing rhu-IL2 (500-1000 U/ml) and rhu-IL15 (20-50 ng/ml) cytokines. Cells are divided when necessary to maintain a cellular concentration of 0.5-1×$10^6$ cell/ml. After 5 days, NK cells activated for 18 hours with IFNα-2b (10-1000 ng/ml, AR09043PU-L, Acris, cells IFNα-NK) or with IL-12 (10 ng/ml, 130-096-798, Miltenyi Biotec) and IL18 (100 ng/ml, 4179-100, Biovision, IL-12/IL-18-NK cells).

Isolation and Cell Expansion—Research-Grade Protocol.

The cell product obtained by leukapheresis is processed using GMP-compliant protocols. The isolation of CD3$^-$CD56$^+$ NK cells is performed with a two-step closed immunomagnetic system consisting in the elimination (negative selection) of CD3$^+$ T cells followed by the positive selection of CD56$^+$ NK cells using the CliniMACS device (151-01, Miltenyi Biotec, Bergisch Gladbach, Germany). All used CliniMACS consumables, plastic material, separation swabs, and tubing sets are manufactured according to GMP standards. Both isolation cycles are performed using the CliniMACS reagents CD3/CD56 complete kit (200-074-01, Miltenyi Biotec) following the manufacturer's instructions. Briefly, cells are washed with phosphate buffered saline (PBS) and diluted with CliniMACS buffer, centrifuged (300×g, 10 minutes at room temperature) and incubated with CD3-specific monoclonal antibodies conjugated with magnetic micro-beads (CliniMACS CD3 reagent, 273-01) for 30 minutes. After incubation, cells are washed with a CliniMACS buffer and placed in the CliniMACS cell separator using the CliniMACS tubing set LS (162-01), performing the DEPLETION 2.1 program. Marked cells are kept in a column using a high-magnetic gradient field. Non-marked cells (CD3-fraction) are collected in the dedicated collection bag. The obtained CD3-fraction in centrifuged and incubated with CD56-specific monoclonal antibodies conjugated with magnetic micro-beads (CliniMACS CD56 reagent, 271-01) for 30 minutes at room temperature, washed and placed in the cell separator using the CliniMACS tubing set (161-01) and the ENRICHMENT 1.1 program available in the CliniMACS device. After separation, cell density and vitality are assessed at the microscope by Trypan Blue exclusion with coloration. Purity is determined by flow cytometry.

The obtained $CD3^-CD56^+$ NK cells are re-suspended in GMP-grade CellGro® SCGM serum-free medium (CellGenix, Freiburg, Germany) supplemented with 5-10% of GMP-grade FBS (Hyclone), and expanded for 24-168 hours with lethally irradiated autologous feeder cells (30Gy, RADGIL irradiator, serial no. 048785002, Gilardoni) (report NK:PBMC=1:(5-20)) obtained from CD3-CD56-cells during the isolation of NK cells, and rhu-IL2 (100-1000 IU/ml—Proleukin, Chiron) and rhu-IL15 (20-50 ng/ml, 1013-050, CellGro®, CellGenix, Freiburg, Germany). Cells are cultured in closed GMP-grade Vuelife® Cell Culture Bags (CellGenix, Freiburg, Germany). Half of the medium is changed every 48 hours with fresh medium and IL2 (100-1000 IU/ml)+IL15 (20-50 ng/ml) cytokines. The IFNα-2b cytokine (10-1000 ng/ml, Schering-Plough Corp.) is added preferably in the last 24 hours of the culture. 25-75% of NK cells are activated with IFNα-2b. Activated NK cells are washed twice with 0.9% sodium chloride saline solution (LAGE 1324, Baxter), and re-suspended in 50-150 ml of Ringer lactate solution (Fresenius Kabi, Verona, Italy) and 2% human albumin (Grifolds, Pisa, Italy) at a cellular concentration to be determined. The total number of cells must be determined and is included in the $10-10000\times10^6$ range. The cell suspension is transferred in the bag and infused to the recipient by gravity drainage through a catheter accessing the portal vein, and introduced under radiological guidance. The remaining 50% of the cellular suspension is expanded in a culture with cytokines IL2 (100-1000 IU/ml)+IL15 (20-50 ng/ml) in order to perform multiple intrahepatic and/or intravenous infusions. The medium is replaced every 2-4 days with fresh medium and cytokines IL2 (100-1000 IU/ml)+IL15 (20-50 ng/ml). Cells are divided when necessary to maintain cell concentration of approximately $0.5-5\times10^6$ cells/ml. Before infusion, cells are activated with IFNα-2b for 24 hours and washed twice with 0.9% sodium chloride saline solution before inoculation. The patient will receive a total of 2-10 infusions for a period of 20-25 weeks (to be determined).

The release of every cell lot is performed only if quality control criteria (sterility, identity, potency, specificity, vitality) are met.

Transfection of Huh7.5 Hepatic Cell Line with HCV JFH1 Replicon.

Plasmid pFK-Luc-JFH1/WT (GT 2a, Apath L.L.C.) is linearized with the Mlu-I restriction enzyme (R0198, NEB) and transcribed in HCV RNA with the MEGAScript® T7 kit (AM1334, ThermoFisher Scientific). Huh7.5 cells (Apath L.L.C.) are transfected with the HCV RNA by electroporation ($3\times10^6$ cells 2.5 µg RNA, buffer SE, CA-138 program, Nucleofector 4D, Lonza).

Production of Viral Stocks.

To generate viral stocks, the supernatant collected from the Huh7.5 cell cultures permanently infected with HCV is collected in tubes and centrifuged at 1000×g per 10 min, at 4° C., and filtered with 0.45 µm filters to remove cell debris. The solution containing the virus is maintained at a pH of approx. 7.55 adding Hepes (20 mM, 17-737, Lonza). Viral particles are concentrated overnight at 4° C. by precipitation adding 4 parts of a Polyethylene-glycol-6000 solution (40%, 25322-68-3, Merck) and NaCl (2.5M, S9888, Sigma-Aldrich). After precipitation, the virus is collected for ultracentrifugation at 4° C., 13000×g for 30 minutes. At the end, the pellet is re-suspended with a minimum volume of phosphate buffered saline (PBS). Aliquots of the virus are stored at −80° C. Each viral stock is titered to establish the TCID50 (50% Tissue Culture Infectious Dose). Briefly, the virus is defrosted and diluted serially in DMEM medium (S1145, Sigma-Aldrich) without serum. Each dilution is used to infect target cells (Huh7.5), plated 24 hours before in the wells of a flat 96-well plate (3599, Costar) at a concentration of 5,000 cells/well. Each well is washed before inoculation with DMEM without serum twice, and the inoculated with 100 µl of each virus dilution. The plate is incubated at 37° C. for 24 hours, after which the inoculum is removed and replaced with 200 µl of complete DMEM with 10% FBS. After 72 hours of infection, the TCID50 level is assessed by immunofluorescence (see below description of the immunofluorescence method).

Infection.

Huh7.5 cells are kept in culture flasks of 75 cm² for 12 days in DMEM medium, 10% FBS, penicillin/streptomycin; L-glutamine enriched with DMSO (1%, 0482, Medical GmbH). The medium is replaced every 3 days. Cells are divided with Trypsin/EDTA (T3924, Sigma-Aldrich) as they reach 80% confluence. Cells are infected with HCV virus with a MOI of 0.03 or with supernatant coming from cultures of infected cells to test their infectivity (when indicated).

NK Co-Cultures with HCV-Infected HepG2, Hep3B, Huh7.5, and Huh7.5 Cells and Immunofluorescence.

$3\times10^4$ target cells HepG2 (BS TCL 79, Istituto Sperimentale Zootecnico della Lombardia ed Emilia Romagna, I.Z.S.L.E.R., Brescia, Italy), Hep3B (86062703, Sigma-Aldrich), Huh7.5 (Apath L.L.C.), and Huh7.5-HCV infected are plated in the lower well of 24-well plates (CC3470, Corning) (when indicated, wells contain coverslips with a diameter of 12 mm-1014355112NR15, ThermoFisher Scientific). In the upper compartment (Transwell porosity 0.4 µm; CC3470, Corning) $3\times10^5$ NK activated cells are plated. After 2, 4, 6/7 days, an aliquot of the culture medium is used to quantify the alpha-fetoprotein (L2KAP2, Medical System) and/or viral load with the HCV Core Ag kit (cat #6L47, Architect, Abbott) following the manufacturer's instructions. On day 6/7, the HCV-infected target cells are fixed in cold Methanol (67-56-1, Merck) for 20 minutes at −20° C., then treated with blocking buffer (PBS, Normal Goat Serum 5% (ab7481, Abcam) BSA (1%, cat #A9418, Sigma-Aldrich)) for 1 hour at room temperature, incubated with monoclonal primary antibody mouse anti-HCV Core [C7-50] (1:300, ab2740, Abcam) 16-18 hours at 4° C., and with the secondary antibody goat-anti-mouse-IgG (H+L)-AlexaFluor568 (1:1000, A11031, Molecular Probes). Slides are mounted on coverslips with ProLong Gold anti-fade containing DAPI for nucleus marking (P36935, Molecular Probes). Images are acquired by confocal microscopy (TCS SP5 II, Leica).

Cytotoxicity Assay.

Target cells are marked with $^{51}Cr$ (2mCi, NEZ030002MC, PerkinElmer) for 16-18 hours and incubated for 4 hours with growing doses of resting NK cells or activated with IFNα or IL12/IL18 in wells of 96-well round plates (3799, Corning Costar). 25 µl of supernatant are transferred to 96-well plates containing scintillation fluid (Lumaplate, cat #6005630, PerkinElmer), and radiations read on MicroBeta2 (2450, Microplate Counter, PerkinElmer). The specific lysis percentage is calculated using the following formula: [(experimental CPM−spontaneous CPM)/(maximum CPM−spontaneous CPM)×100], "CPM"

indicating the "Count (of Chrome51) Per Minute" released in the culture medium. All assays are repeated three times.

In Vivo Experiment on uPA/SCID Animal Model.

Two-week-old uPA/SCID mice [23] are transplanted intrasplenically with primary human hepatocytes (HH223, Lonza). After 12 weeks, the mice receive an intraperitoneal dose of $2 \times 10^4$ ffu (focus-forming unit) of H77 virus (GT1a). Mice receive two intrasplenic doses of NK cells, one on the day following the infection ($2 \times 10^7$), the second after one week ($1 \times 10^7$). The viral load (HCV RNA, RT-PCR, University of Ghent) and the serum levels of human albumin (in-house sandwich ELISA, University of Ghent, as previously described [23]) are monitored weekly with a blood test of the blood withdrawn from the tail. Mice are sacrificed after 6 weeks and the liver procured is, a part kept in formalin for hystological analysis, and a part kept in Trizol (700 ml, cat #10296-010, Invitrogen) and stored at $-80°$ C. for the subsequent gene expression analysis.

Gene Expression and HCV RNA Amplification.

In order to assess the levels of gene expression of the CD56 gene, fresh liver tissue samples have been defrosted and homogenized with lysis buffer by TissueLyser LT (Qiagen) using steel beams with a 3-mm diameter. The obtained lysate was used for total RNA isolation by RNeasy Protect Mini kit (cat #74124, Qiagen) following the kit specifications. The obtained RNA was reverse-transcribed in cDNA by High Capacity cDNA Reverse Transcription kit in a total reaction volume of 20 µl containing 10×RT Buffer, 10×RT random primers, 25×dNTP mix (100 mM), Multiscribe Reverse Transcriptase 50 U/ml, and RNAse inhibitor (cat #4368814, Applied Biosystems). The reverse transcription was performed according to the following thermal profile: $25°$ C. for 10 minutes, $37°$ C. for 120 minutes, and $85°$ C. for 5 minutes. The obtained cDNA was pre-amplified using the TaqMan PreAmp Master Mix kit (cat #4391128, Applied Biosystems) with the following thermal profile: $90°$ C. for 10 minutes followed by 10 cycles at $95°$ C. for 15 seconds, and $60°$ C. for 4 minutes. The obtained pre-amplified cDNA was used to assess the expression profile of the CD56 gene by Realtime PCR, using TaqMan Gene Expression Assay and Gene Expression Master Mix (cat #4369016, Applied Biosystems). The experiment was repeated three times on the 7900 HT Fast Real Time PCR System (Applied Biosystem) with the following thermal profile: $95°$ C. for 10', 50 cycles at $95°$ C. for 15", and $60°$ C. for 1'. The levels of gene expression of the CD56 gene were obtained by relative quantization ($2^{-\Delta\Delta C_t}$) using the gene house-keeping GAPDH for normalization, and comparing data obtained from treated mice (K1872R and K1872L treated with IFNα-NK; K1848 and B1191L with IL12/IL18-NK) with the data obtained from naive mice (B1193R) and used as calibrator. For quantification of HCV RNA levels, the HCV RNA was isolated and amplified with a COBAS AmpliPrep/COBAS TaqMan system (cat #HCVQTV2, Roche Diagnostic, Manheim, Germany) (range $\leq 1.50E+01$ IU/ml–$\leq 1.00E+08$ IU/ml). The samples were analyzed three times and the viral load was expressed in IU/ml.

Histology.

Samples fixed in formalin are dehydrated (75%, 95%, 100% ethanol and xylene) and included in paraffin. 5 µm sections are cut with microtome, dewaxed, and rehydrated (xylene, ethanol 100%, 95%, 75% and water). To visualize the viral proteins, sections are balanced in PBS, the antigen is unmasked with enzymatic digestion (cat #Ab970, Abcam), processed with blocking "mouse-on-mouse" (MOM kit, ImmPRESS Peroxidase Polymer, cat #MP-2400, Vector Lab), endogenous biotin block (avidin/biotin kit, ab64212, Abcam), blocked with blocking solution (MOM kit, ImmPRESS Peroxidase Polymer, cat #MP-2400, Vector Lab), blocked with PBS+Normal Horse Serum (NHS, kit Vectastain Elite ABC, MouseIgG, cat #PK-6102, Vector Lab), and incubated overnight with the mouse primary antibody anti-HCV NS3 (clone MMM33, cat #MONX11007, Monosan) in PBS/NHS at $4°$ C. in humidified chamber. After 5 washes in PBS/0.05% Tween-20, sections are processed with 3% H2O2 (endogenous peroxidase block), incubated with secondary biotinylated and avidin antibody—HRP (kit Vectastain Elite ABC, MouseIgG, cat #PK-6102, Vector Lab) and DAB sublayer (cat #SK-4100, Vector Lab) following the manufacturer's instructions. To visualize the NK cells, sections are processed with sodium citrate dehydrate 10 mM, 0.05% Tween 20, pH 6.0 to unmask the antigen (three 50' cycles, power 50P microwaves), blocked for endogenous biotin (avidin/biotin kit, ab64212, Abcam), blocked with PBS+Norma Goat Serum (10%, ab7481, Abcam), and incubated overnight with primary antibody rabbit anti-human CD56 (1:1000, clone EP2567Y, NBP1-40520, NovusBio). After washing 5 times in PBS/0.05% Tween-20, sections are processed with 3% H2O2 (block endogenous peroxidase), incubated with secondary biotinylated and avidin antibody—HRP (Rabbit IgG, Vectastain Elite ABC, cat #PK-6101, VectroLab) and DAB substrate (Vector Lab) following the manufacturer's instructions. Nucleuses are counterstained with hematoxylin. Images are obtained by clear-field microscopy (Olympus CKX41).

Results

Isolation and Expansion of NK Cells from Liver Perfusate

Figure 3A:
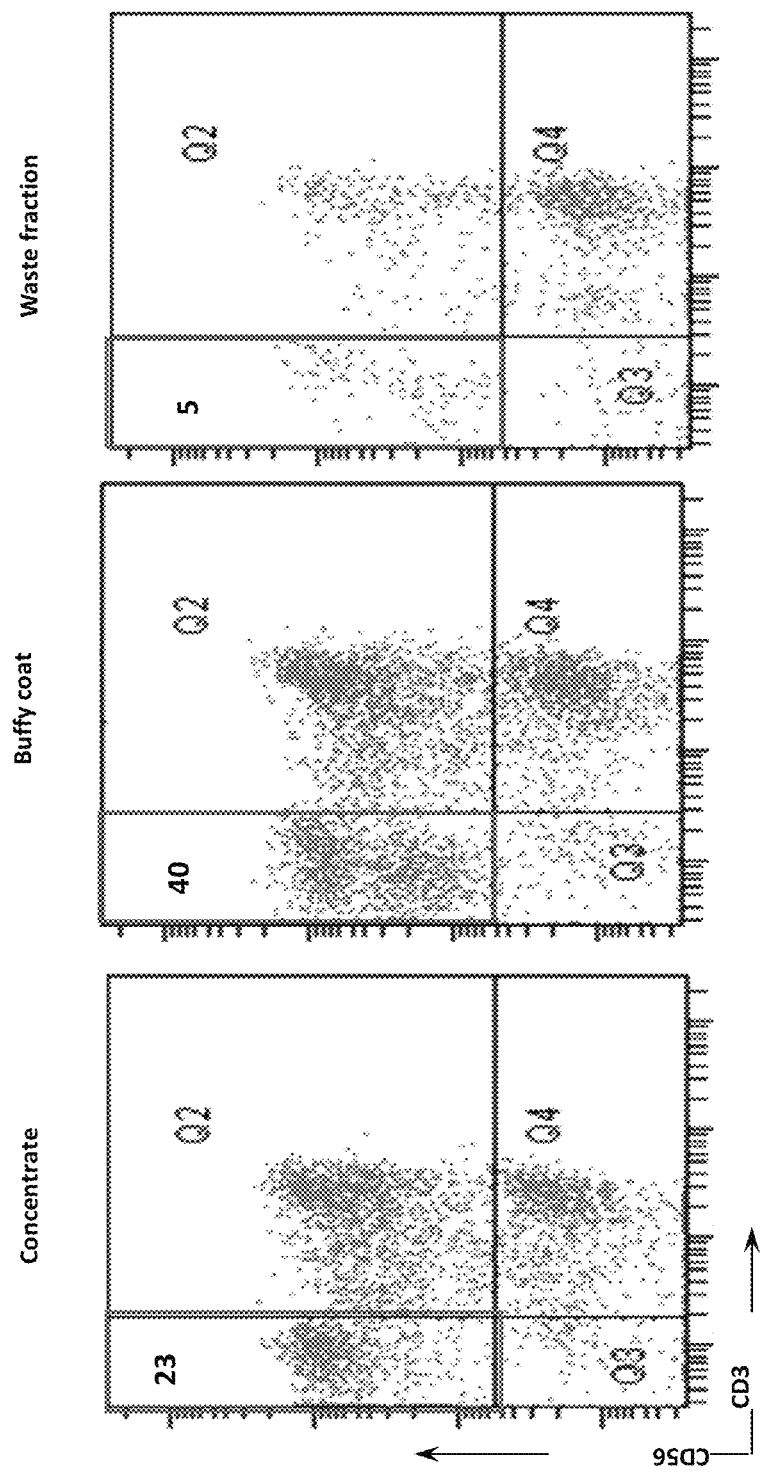
FIG. 3: Isolation and expansion of NK cells from liver perfusate. Flow cytometry for surface markers CD45, CD3, and CD56 of liver perfusate leukapheresis fractions (3a, concentrate, buffy coat, and waste), and after magnetic selection (3b, buffy coat, CD3$^+$, CD3$^-$, CD3$^-$CD56$^+$ fraction). (3c) Phenotype for activation markers CD16, NKp30, NKp44, and NKp46, and for the presence of contaminating CD3$^+$ T cells in the CD3$^-$CD56$^+$ NK cell cultures after isolation (ex vivo), and after 14 days of expansion with feeder cells and maintenance cytokines IL2/IL15. (3d) NK cell growth curve. In three weeks of culture, the number is increased by 400 times. (3a-3c) Numbers in the "dot-plot" diagrams indicate the percentage of the single cell populations. Data are representative of at least 20 (3a, 3b), 5 (3c), and 3 (3d) experiments repeated in equivalent conditions.
Figure 3B:
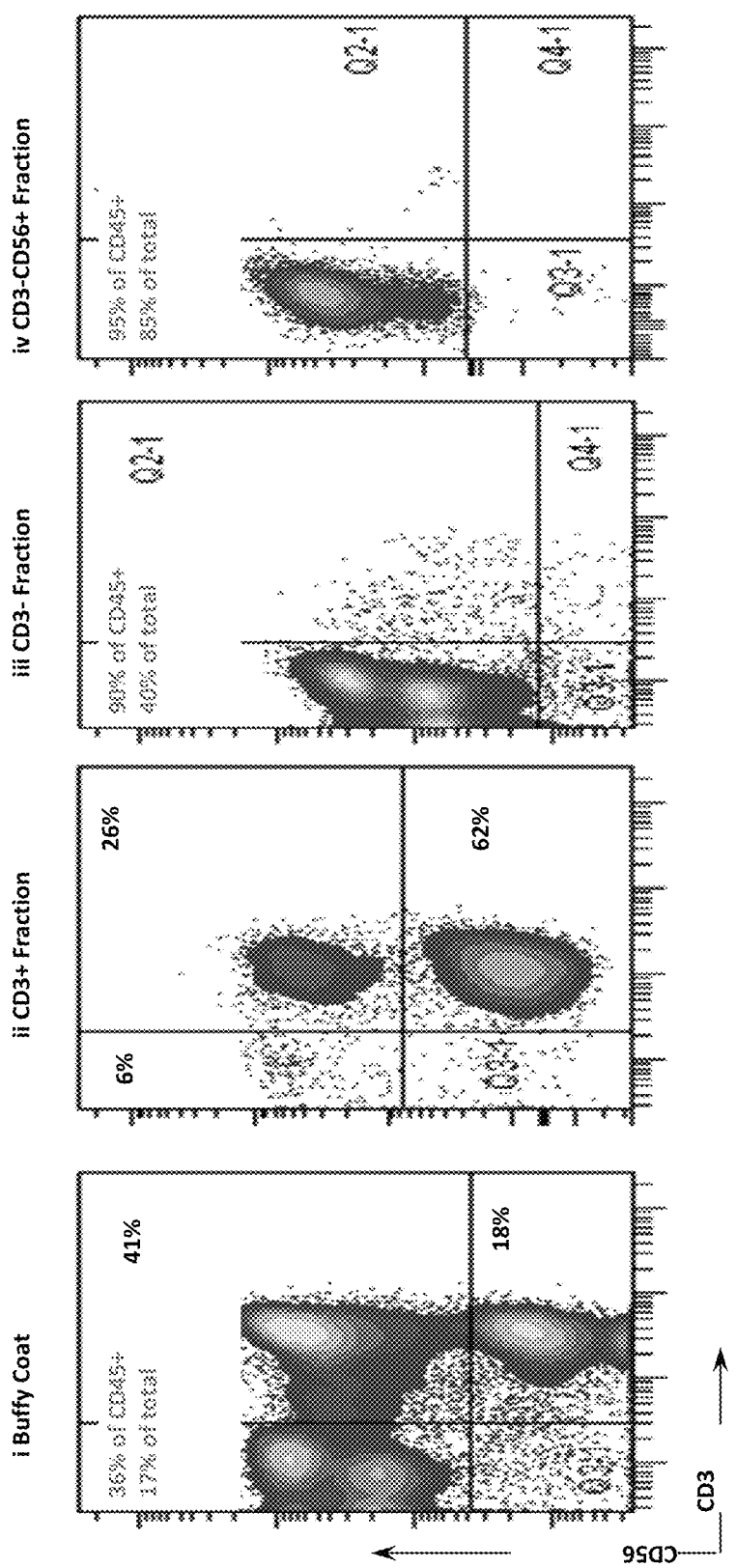

Donor's liver perfusate is delivered at a controlled temperature ($4°$ C.) to research laboratories at the time of liver transplant. The perfusate consists of a flush in Celsior solution and 10% ACD of the liver vasculature blood in order to minimize the damage caused by coagulation of the organ after the removal. The volume of the perfusate, a biological fluid similar to diluted whole blood, is on average 5-8 liters. By centrifugation, the volume is reduced to approximately 0.5-1.5 liters. The buffy coat is isolated from the perfusate by apheresis. The Com.TEC apheresis platform can process whole blood with a physiological hematocrit level (HCT=30-45%). Centrifugation allows concentrating the initial perfusate and obtaining an HCT level adequate for the apheresis (initial HCT=6-15%; final HCT=35-45%). The apheresis allows to effectively isolate whole blood mononuclear cells by means of repeated cycles of concentration and collection. 4-8 collection cycles are performed to make sure only a few cells of interest are lost in the waste fraction. FIG. 3a shows the phenotype of the initial fraction (concentrated), the buffy coat and the waste fraction highlighting the percentage of NK cells indicated by the CD3$^-$CD56$^+$ phenotype. The fraction of the buffy coat is enriched for NK cells (40% in buffy coat vs. 23% in concentrate and 5% in waste fraction), while a marginal loss is present in the waste. This confirms the effectiveness of the enrichment procedure for the relevant cell fraction. The number of cells obtained from the liver perfusate ranges from 1 to $25 \times 10^9$, based on individual variability. The sample is processed with ACK solution to lyse red blood cells. Residual platelets are eliminated by mild centrifugation (200×g, 10 minutes, $20°$ C.). NK cells are purified by cell separation mediated by monoclonal antibodies conjugated to magnetic beads and magnetic field (Miltenyi Biotec technology). Separation involves two steps: a first step to eliminate CD3$^+$ cells (FIG. 3b-ii, negative selection). The efficiency of CD3$^+$ cell depletion is very high as shown in FIG. 3b-iii, where a contamination of <1% residual CD3$^+$ cells can be seen. It is important to eliminate CD3+ T-cells as they are responsible for causing Graft-Versus-Host-Disease (GvHD) in the recipient, in case of allotransplant. According to recent guidelines, the maximum number of tolerated CD3+ T-cells in case of allotransplant must be below $0.1 \times 10^6$ T cells/Kg [14]. In the second step of magnetic selection, from the obtained CD3− fraction, CD56+ cells are isolated (FIG. 3b-iv, positive selection).

Figure 3C:
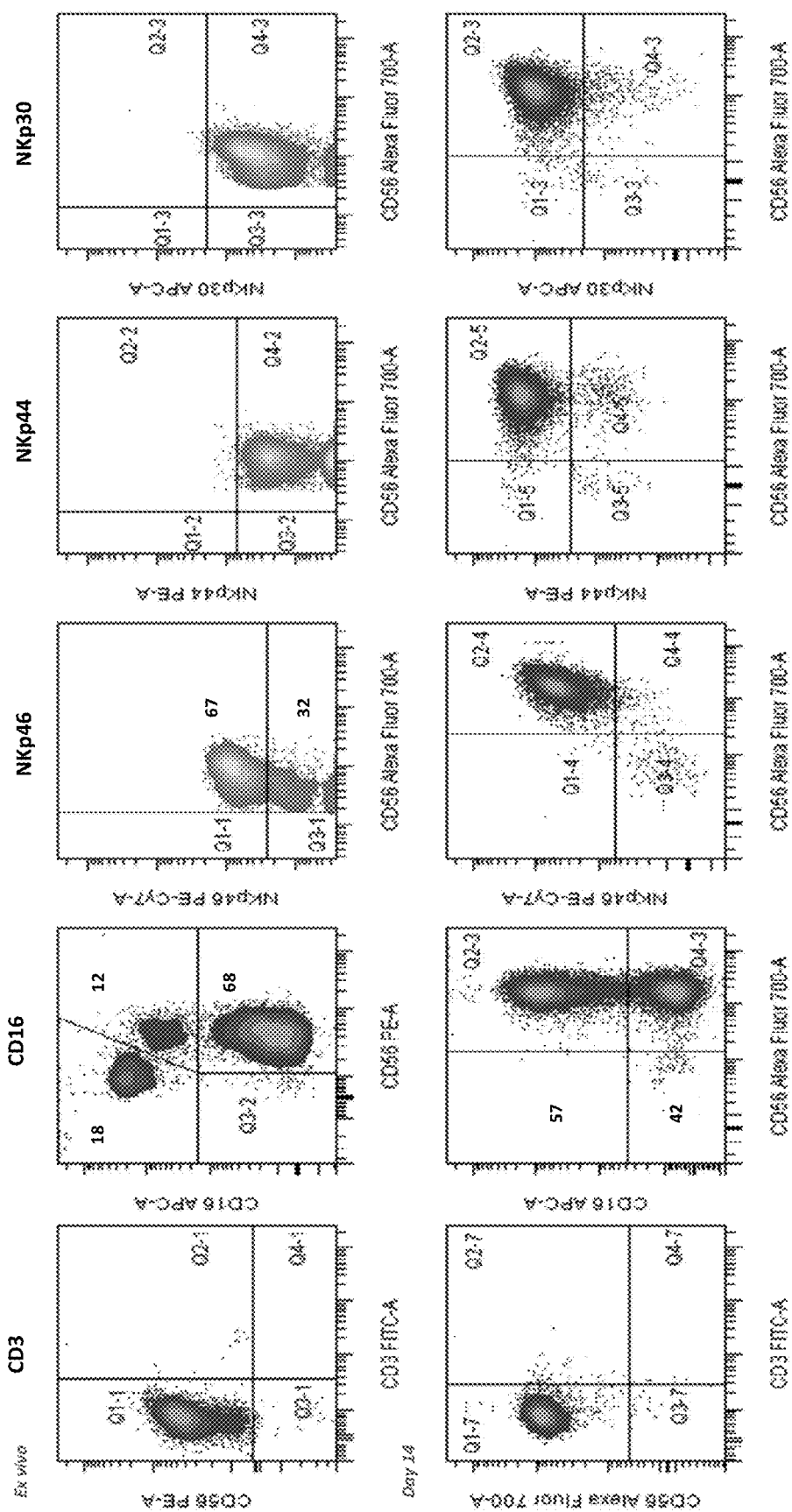
Figure 3D:
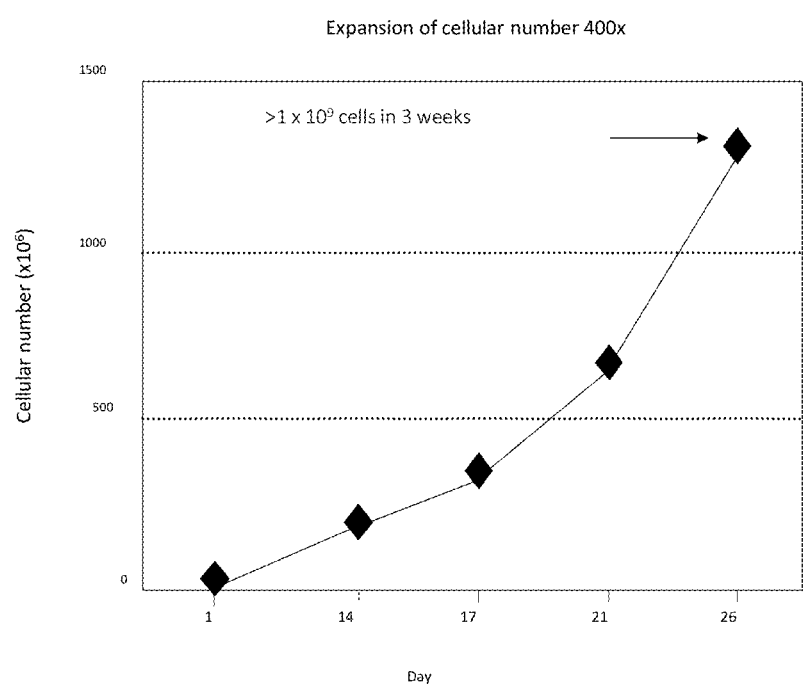

The number of initial cells is very high ($1\text{-}25 \times 10^9$). In the present invention, two systems for CD3−CD56+ NK cell isolation are used. For large-scale isolation, in compliance with GMP standards, the CliniMACS tools (Miltenyi Biotec) is used. For in vitro characterization experiments, it is sufficient to perform the selection using research-grade reagents and tools, such as AutoMACS, for automated procedure and large-scale isolations, or QuadroMACS for manual isolation and small-scale isolations (Miltenyi Biotec). CD3−CD56+ NK cells are expanded in the presence of irradiated feeder cells (K562 or PBMC) and growth factors [IL2+IL15], thus obtaining in 3 weeks an average increase in the number of cells by 400 times (FIG. 3d). The phenotype of expanded cells is checked to verify the presence of unwanted contaminating CD3+ cells, which are indeed absent (ex vivo and day 14, FIG. 3c). The phenotype of the NK cells is characterized ex vivo (panels above, FIG. 3c) and after 14 days of culture with feeder cells and cytokines (panels below, FIG. 3c). More specifically, the expression of surface markers delineating an activated phenotype indicated by the expression of CD16, NKp30, NKp44, NKp46 molecules was studied (FIG. 3c). After expansion/activation, NK cells show an activation phenotype with expression of the above-mentioned surface markers involved in the innate response.

Freezing/thawing cycles do not alter the phenotype or cell function (date not shown), therefore allowing the production of a biobank. The possibility to stock NK cells is necessary to plan repeated infusions.

In Vitro Activation of NK Cells

NK cells respond to cytokines involved in the immune response such as IFNα [24], IL12 and IL18 [25, 26]. Two different activation protocols were tested to study the functionality of NK cells in tumor response and infection. NK cells show a different phenotype based on the type of activation:
1) activation with cytokine IFNα induces a "cytotoxic" phenotype, with up-regulation of the surface protein TRAIL. TRAIL is involved in the induction of death by apoptosis of target cells that express its specific ligand (FIG. 4a) [24]. The expression of the TRAIL molecule occurs already after a few hours of stimulation with IFNα (4 hours, FIG. 4b) and remains stable over time (18 hours, FIG. 4b).
2) activation with the combination of cytokines [IL12+IL18] induces NK cells release of cytokines, such as IFNγ and TNFα, but not TRAIL expression, mediating the anti-cancer and anti-viral function of NK cells mainly through soluble factors (FIG. 4a) [25, 26]. Similarly, maintenance cytokines [IL2+IL15] induce the production of pro-inflammation soluble factors, even if less efficiently than the combination [IL12+IL18] (FIG. 4a).

Figure 4C:
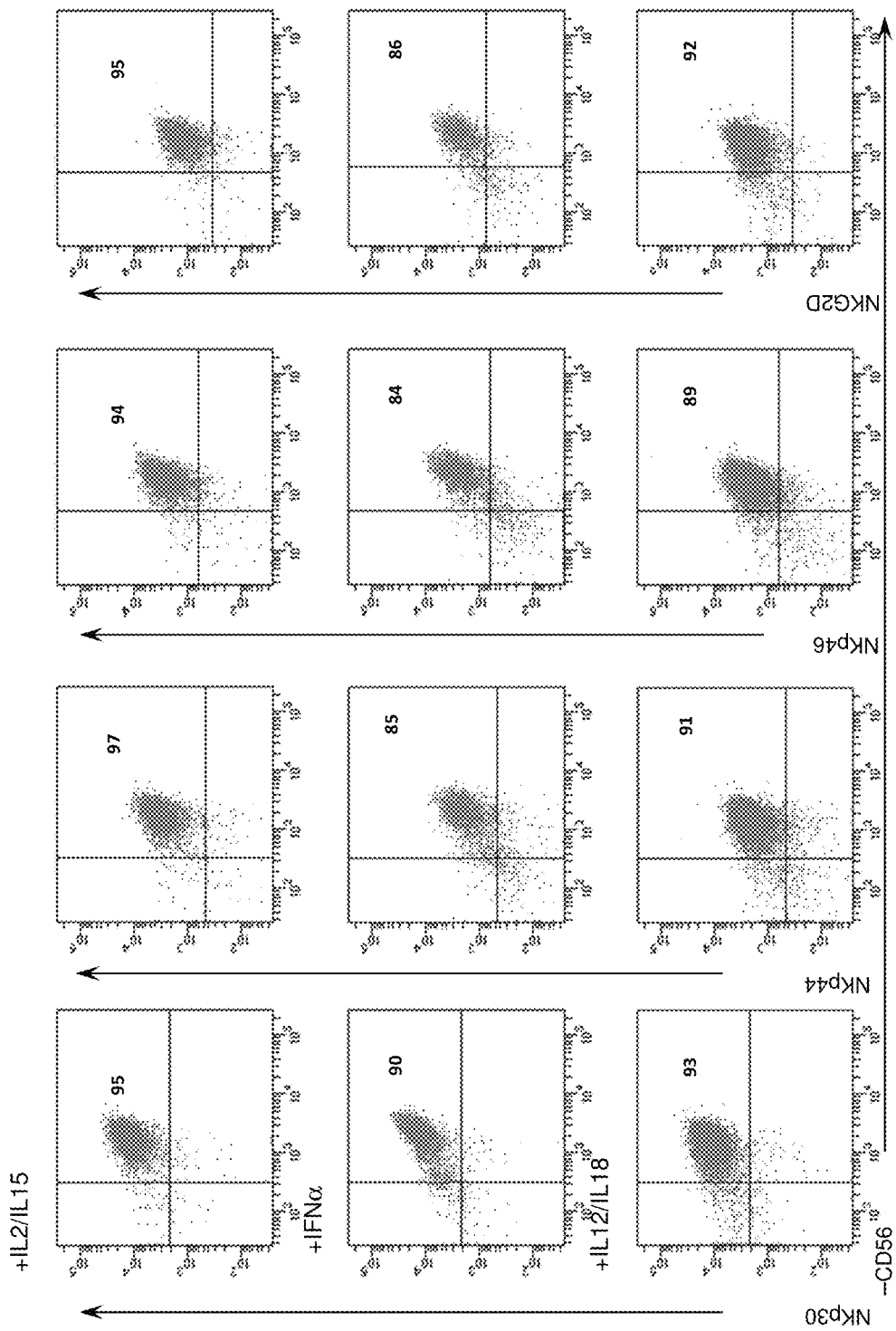
FIG. 4: NK cell differentiation and phenotype characterization. (4a) Flow cytometry of CD56$^+$ NK cells for surface marker expression of TRAIL and for production of proinflammatory cytokines IFN-γ and TNF-α by means of intracellular marking after activation with growth factors IL2/IL15, IFNα or IL12/IL18. (4b) NK cells express the TRAIL surface marker 4 hours after activation with IFNα, and the expression lasts another 18 hours after activation. (4c) Phenotype characterization of activated NK cells with a cocktail of cytokines IL2/IL15 or IFNα or IL12/IL18. Activation markers NKp30, NKp44, NKp46, and NKG2D are regularly expressed in all tested conditions. (4a-4c) Numbers in the "dot-plot" diagrams indicate the percentage of single cell populations. Data are representative of at least 3 experiments repeated in equivalent conditions.

Finally, the level of expression of known activation markers such as cytotoxicity receptors NKp30, NKp44, NKp46 and activation receptor NKG2D, were characterized, observing that the phenotype of NK cells after stimulation with [IL2+IL15], IFNα, and [IL12+IL18] is very similar in all experimental conditions (FIG. 4c).

In Vitro and In Vivo Antiviral Function of NK Cells

Figure 5A:
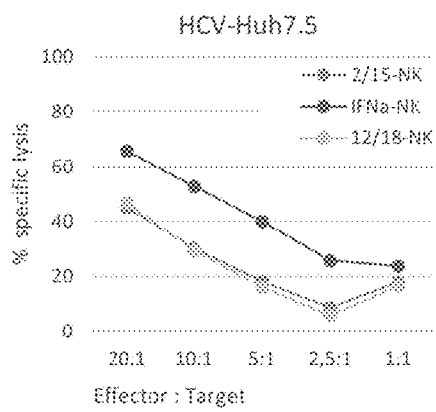
FIG. 5: Study of NK cell antiviral function. (5a) Cytotoxicity assays with radioactive Chromium 51 of preactivated NK cells with IL2/IL15 (green), IFNα (blue) or IL12/IL18 (yellow) using as target cells Huh7.5 tumor cell lines infected with HCV. The specific lysis percentage is calculated with the following formula: [(experimental CPM−spontaneous CPM)/(maximum CPM−spontaneous CPM)×100], where "CPM" indicates the "Counts (of Chromium51) Per Minute" released in the culture medium. Radioactivity is measured by a gamma counter. (5b-5d) Huh7.5 target cells infected with HCV are grown on 24-well plates for 6 days with NK cells placed on Transwell inserts to prevent contact between target and effector cells. NK cells are previously activated with IL2/IL15, IFNα or IL12/IL18. As controls, in one well, no NK cells were plated. The antiviral effect of NK cells is evaluated: (5b) by immunofluorescence, tracking of HCV Core antigen expression present in target cells. HCV Core antigen is detected through a specific antibody conjugated with Alexa-568 fluorochrome (red); nuclei are counterstained with DAPI (blue) (magnification 200×); (5c) through quantification of HCV Core antigen present in the culture medium after a combined culture with NK cells. The chart shows the concentration values of viral antigen detected and normalized with respective untreated control (n=8). The reduced HCV Core production after treatment with IFNα-NK cells is statistically significant compared to the use of IL2/IL15-NK (**) and IL12-IL18-NK (*, unpaired t test); (5d) by assessing the culture medium infectivity after treatment with NK cells on Huh7.5 naïve cells. HCV Core antigen released by infected cells is quantified 6 days after infection with the supernatant. The reduced infectivity of the supernatant of the target cells treated with NK cells is statistically significant compared to untreated sample (unpaired t test). Differences with $P<0.05$ are considered significant. Data (5a, 5b) and (5d) are representative of 5 and 3 individual experiments, respectively, repeated in similar conditions. (5e-5h) uPA/SCID mice transplanted with human hepatocytes and infected with HCV receive two cycles of NK-mediated immunotherapy: n=2 with IFNα-NK; n=2 with IL12/IL18-NK; n=2 no therapy. A control mouse died before the end of the experiment. (5e) Viremia is quantified at the end of the experiment. Mice receiving IFNα-NK cells show lower viremia values (squares), whereas untreated mice (circles) and mice receiving IL12/IL18-NK cells (triangles) have higher viremia values (highlighted in the grey zone). (5f) Human albumin values in the mouse blood registered no significant variations for the entire duration of the experiment. Values are shown before the infection (week −1) and at the end of the experiment (week 6). Each symbol represents a mouse. (5g) qRT-PCR on liver samples of single mice to quantify infiltration of NK cells (by CD56 gene amplification, green square, right axis), and infection rate (viral RNA amplification, red circle, left axis). Mice treated with IFNα-NK are highlighted in red to show that an increased intrahepatic infiltration of NK cells correlates with a lower viremia. (5h) Histology on liver sections of mice with specific CD56 antibody to evaluate infiltration of NK cells, or specific virus NS3 protein antibody to evaluate the rate of infection. One representative mouse for each group of treatment is shown. Human hepatocytes (H, white cells) are morphologically different from mouse hepatocytes (M, blue cells) (magnification 200×).
Figure 5B:
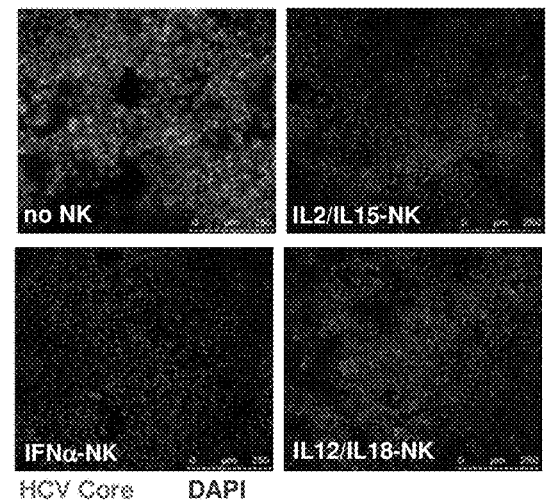
Figure 5C:
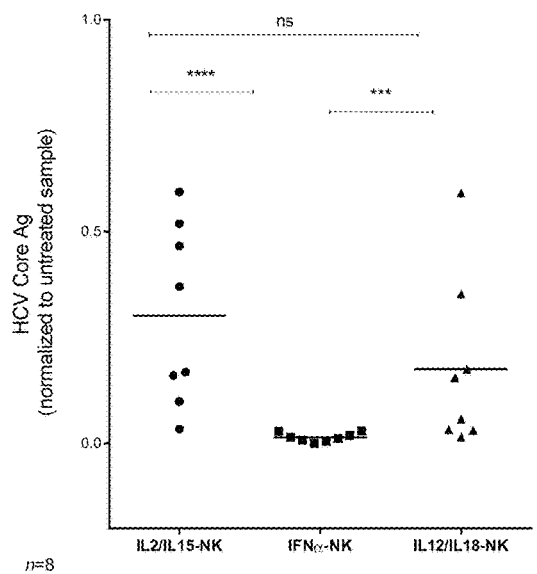

The phenotypic variation observed after the stimulation with different cytokine mix implied also a different activity of NK cells themselves with regard to target cells. To validate this hypothesis, the cytotoxic function of NK cells activated with the two different protocols was tested using as target cells cell lines of human liver cancer infected with HCV. FIG. 5a shows the cytotoxicity of NK cells cultures with maintenance cytokines [IL2+IL15] (hereinafter referred to as "resting," green), or activated with IFNα (blue) or with the mix [IL12+IL18] (yellow). Activation with IFNα induces an improvement of the cytotoxic function of NK cells in the presence of HCV infection. Cells activated with [IL12+IL18] show still a valid cytotoxic function, but less efficient than IFNα-NK and overlapping with the resting NK cells. This result confirms that the activation with IFNα increases the cytotoxicity of NK cells, as reflected by the phenotype analysis. During viral infection, NK cells produce soluble factors as a response to the infectious agent. The response of NK cells mediated by cytokines was determined by means of co-cultures of effector NK cells and target cells Huh7.5 infected with HCV, using Transwell inserts as a physical barrier to prevent contact between effector and target cells. The Transwell inserts used in this experimental setting had a porosity of 0.4 μm thus not allowing the passage of cells but ensuring the exchange of soluble factors. As demonstrated in FIG. 5b, NK cells have an antiviral effect mediated by soluble factors that greatly depends on the activation protocol. NK cells stimulated with IFNα have an antiviral effect considerably higher than NK cells activated with [IL12+IL18] or than resting NK cells. By means of immunofluorescence, the inventors showed the presence of HCV virions inside target cells using a monoclonal antibody specific for the Core viral antigen (red, FIG. 5b). HCV-Huh7.5 cells after 6 days of co-culture with IFNα-NK show infection levels visibly reduced compared to naive cells, or with those in co-culture with resting NK cells or IL12/IL18-NK (FIG. 5b), where the fluorescence marking the viral antigen is clearly visible, even if with a less frequency compared with control cells (HCV-Huh7.5 cell not treated with NK cells). These data are corroborated by quantification assays of HCV Core antigen released in the culture medium. Treatment with IFNα-NK cells significantly reduces the viral load in the medium compared with treatment with IL12/IL18-NK (*) or IL2/IL15-NK (**) (FIG. 5c). Figure 5c shows also the significance of the antiviral effect obtained by activating NK cells with IFNα since the viral clearance is virtually equal to 100% and homogeneous in the whole patient population (n=8). On the contrary, the reduction in viral antigen detected after treatment of the target cells with IL2/IL15-NK and IL12/IL18-NK is heterogeneous because of the individual variability of studied patients.

Figure 5D:
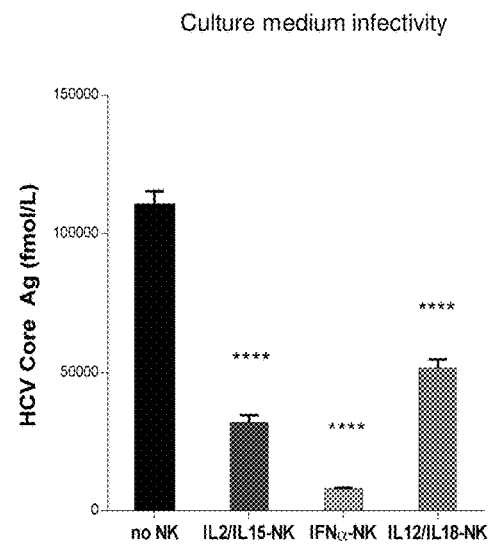
Figure 5H:
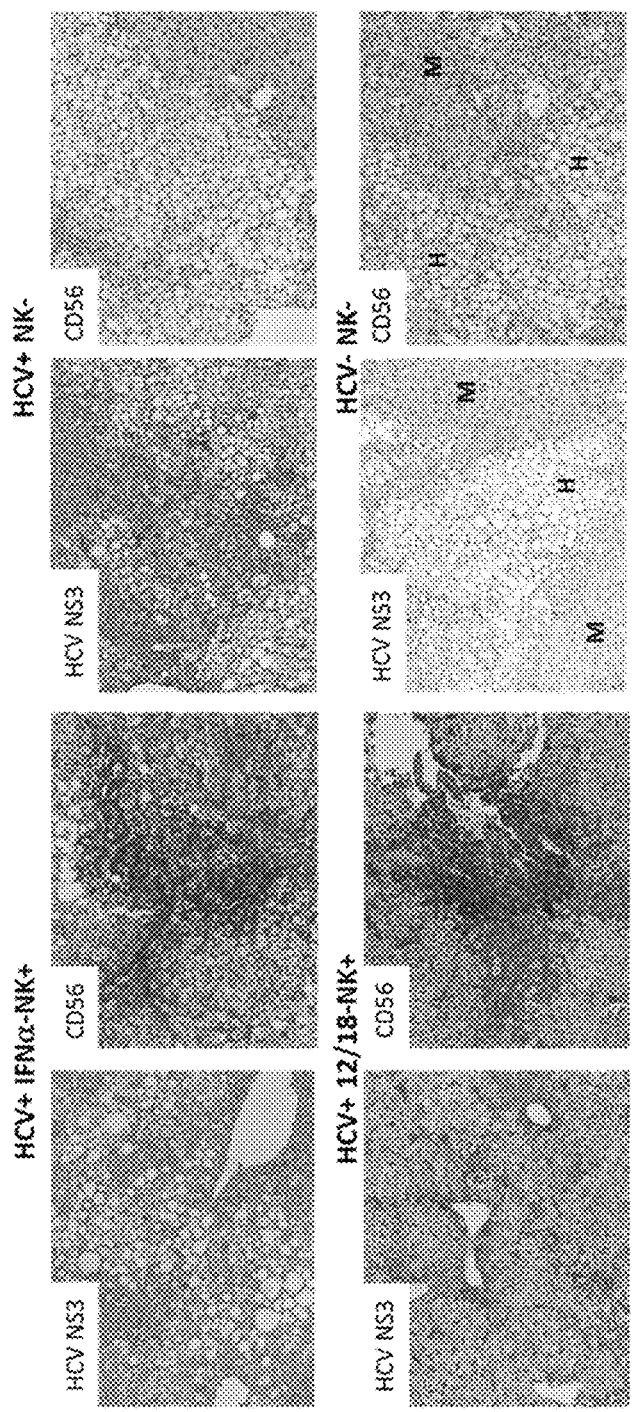

Infectivity of the culture media was tested after the co-culture of Huh7.5-HCV infected cells with resting NK cells, IFNα—NK and IL12/IL18-NK in transwell. Naïve Huh7.5 cells (i.e., not infected) were exposed to these culture media for 18 hours, then medium was removed and replaced with fresh medium. Viral load was then quantified after 3 days. As shown in FIG. 5d, treatment with IFNα-NK was more effective in reducing the infectivity of the culture medium compared with the use of NK cells activated with IL2/IL15 and IL12/IL18. All these data strongly suggest that IFNα-NK cells present a higher antiviral potential compared with other tested NK cells. Data obtained in vitro show that it is possible to improve the antiviral function of NK cells by specific activation. In order to validate these in vitro results, the inventors have studied the therapeutic function of NK cells in an animal model that supports HCV infection. They used uPA/SCID mice characterized by a genetic mutation that causes a metabolic syndrome that is toxic for endogenous murine hepatocytes, which are eventually depleted. Mice, with genetic SCID background, can be transplanted with human hepatocytes that exclusively colonize the liver niches made available after degeneration of murine hepatocytes. Chimeric mice can be infected with HCV leading to an active infection[8]. In order to test the protective function of NK cells, infected mice have been treated with two infusions, at a one week interval, of IFNα-NK cells (n=2) or IL12/IL18-NK cells (n=2) and the antiviral function was determined by weekly tracking the viral load. Mice treated with IFNα-NK are characterized by lower viremia levels compared with mice treated with IL12/IL18-NK or naïve mice (n=2, one of the two mice died prematurely) (FIG. 5e). The levels of human albumin in the plasma of mice at the beginning and end of the experiment showed variations falling within the physiological parameters, thus suggesting that mice are not suffering from metabolic alteration and therefore NK cells are not toxic for the organism (FIG. 5f). After 6 weeks from the last NK cell infusion, mice were sacrificed and organs collected for analysis. By means of Real-Time PCR, the level of intrahepatic infiltration of NK cells was quantified amplifying the CD56 marker gene specific for human NK cells (FIG. 5g, green square, right y axis). On the same liver extract, the levels of infection was assessed by amplifying sequences of the HCV genome (FIG. 5g, red circle, left y axis). In FIG. 5g these values are reported on the same chart for each mouse, supporting the evidence that a greater NK cell infiltration correlates with lower levels of infection. Furthermore, as observed with serum viral load results, mice treated with IFNα-NK show the highest levels of infiltrating NK cells and the lowest number of viruses in the liver district. The data was confirmed by immunocytochemistry on sections of mice treated with CD56-specific and HCV NS3-specific antibodies. Histology confirms the infiltration of $CD56^+$ NK cells and the presence of HCV inside human hepatocytes (H, FIG. 5h), visibly distinct from murine hepatocytes (M), as demonstrated by others [23]. A mouse representative of each group is shown in FIG. 5h.

In Vitro Anticancer Function of NK Cells

In parallel, a protocol of optimal activation was studied to increase anticancer activity of NK cells. The cytotoxicity of resting NK cells ([IL2+IL15]) or NK cells activated with IFNα or [IL12+IL18] was tested by means of chrome release against three different cell lines of HCC: HepG2, Hep3B, and Huh7.5.

Figure 6A:
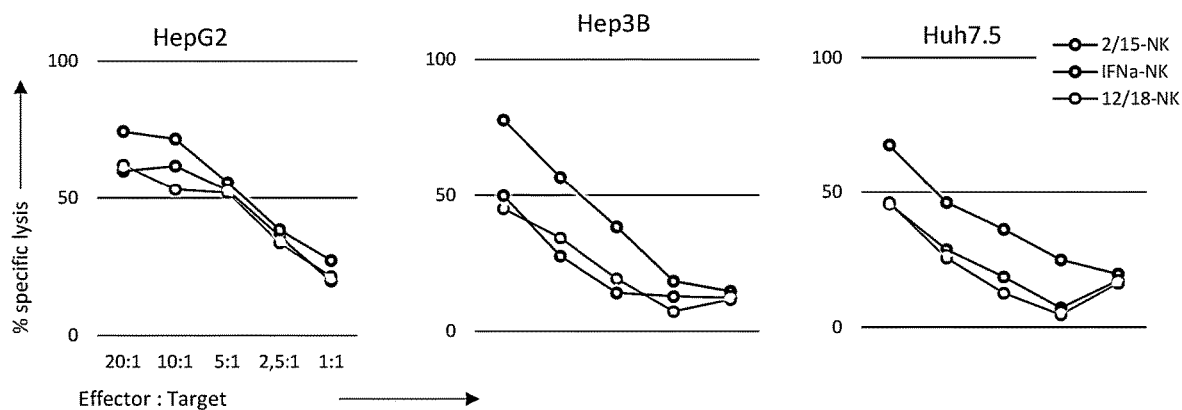
FIG. 6: Antitumor function of NK cells. (6a) Chromium release assay. IL2/IL15-NK (green), IFNα-NK (blue), and IL12/IL18-NK (yellow) cells are tested with increasing doses as effector cells versus three different target cell lines of HCC: HepG2, Hep3B, and Huh7.5. Cytotoxicity is expressed as specific lysis %. Data are representative of 3 experiments conducted in similar conditions (6b) Quantification of alpha-fetoprotein tumor biomarker in HepG2 (n=2), Hep3B (n=2), and Huh7.5 (n=5) medium after 7 days of co-culture with IL2/IL15-NK, IFNα-NK, and IL12/IL18-NK added in Transwell inserts. Alpha-fetoprotein values are expressed as a variation amount normalized to the untreated sample. Statistical analysis is carried out with one way ANOVA versus untreated target cells.
Figure 6B:
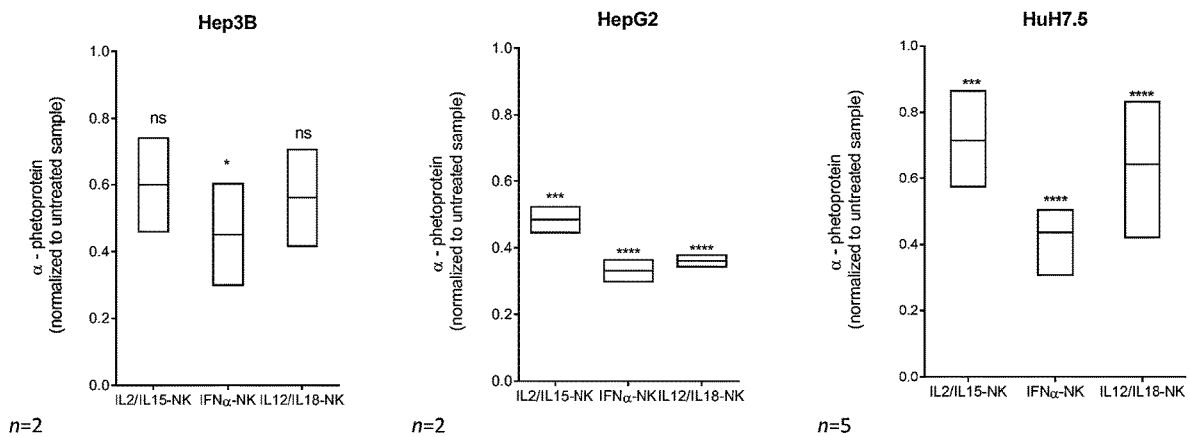

In each condition, the activation with IFNα (blue) proved more effective than the use of cytokines IL2/IL15 (green), and IL12/IL18 (yellow), since a higher degree of specific lysis was seen in all cell lines (FIG. 6a). To identify the potency of the soluble factors released by NK cells based on the activation protocol, resting NK, IFNα-, and IL12/IL18-NK cells were co-cultured in Transwell inserts with target cells HepG2 (n=2), Hep3B (n=2), and Huh7.5 (n=5). After 7 days, the levels of a hepatic tumor biomarker known as alpha-fetoprotein (αFP) were quantified in the culture medium. Compared with the control sample of naïve cancer cells, the quantity of αFP is lower in the presence of NK cells in Transwell inserts, and the most significant reduction in all cell lines was seen in the presence of NK cells activated with IFNα (FIG. 6b).

CONCLUSIONS

The data of the present invention show that NK cell function can be directed towards a more efficient antiviral and antitumor phenotype, using a specific protocol. The activation with cytokines [IL2+IL15] and [IFNα] induces the most efficient NK cell anti-HCV and anti-HCC activity when compared to the cytokine cocktail [IL2+IL15] and [IL12+IL18] or with the only combination of [IL2+IL15].

The present invention NK cell extraction protocol is advantageous compared with the methods used in clinical trials known in literature that use NK-mediated therapies. NK cells are not isolated from the peripheral blood, but from liver perfusate, from which more cells can be obtained not only because there is more starting material available (0.5-1.5 liters compared with the ml obtainable from peripheral blood), but also because NK cells are highly present in the liver compared to other organs (30-50% in the liver compared to 5-15% in the peripheral blood) [12]. The possibility of isolating large numbers of NK cells at the time of the liver transplant is a unique clinical and therapeutic advantage because a timely treatment makes a difference in the prevention of HCV and HCC recurrence.

REFERENCES

1. Schwartz, J. and R. Carithers, *Epidemiology and etiologic associations of hepatocellular carcinoma*. uptodate.com, 2016.
2. Rehermann, B., *Pathogenesis of chronic viral hepatitis: differential roles of T cells and NK cells*. Nat Med, 2013. 19(7): p. 859-68.
3. Lontok, E., et al., *Hepatitis C virus drug resistance-associated substitutions: State of the art summary*. Hepatology, 2015. 62(5): p. 1623-32.
4. Reig, M., et al., *Unexpected high rate of early tumor recurrence in patients with HCV-related HCC undergoing interferon free therapy*. J Hepatol, 2016. 65(4): p. 719-26.
5. Chok, K., *Management of recurrent hepatocellular carcinoma after liver transplant*. World J Hepatol, 2015. 7(8): p. 1142-8.
6. Forns, X., et al., *Antiviral therapy of patients with decompensated cirrhosis to prevent recurrence of hepatitis C after liver transplantation*. J Hepatol, 2003. 39(3): p. 389-96.
7. Thomas, R. M., et al., *Infection with chronic hepatitis C virus and liver transplantation: a role for interferon therapy before transplantation*. Liver Transpl, 2003. 9(9): p. 905-15.
8. Garcia-Retortillo, M., et al., *Hepatitis C virus kinetics during and immediately after liver transplantation*. Hepatology, 2002. 35(3): p. 680-7.
9. Bodduluru, L. N., et al., *Natural killer cells: the journey from puzzles in biology to treatment of cancer*. Cancer Lett, 2015. 357(2): p. 454-67.
10. Sun, C., et al., *Natural killer cell dysfunction in hepatocellular carcinoma and NK cell-based immunotherapy*. Acta Pharmacol Sin, 2015. 36(10): p. 1191-9.
11. Sachdeva, M., Y. K. Chawla, and S. K. Arora, *Immunology of hepatocellular carcinoma*. World J Hepatol, 2015. 7(17): p. 2080-90.
12. Jonsson, J. R., et al., *Human liver transplant perfusate: an abundant source of donor liver-associated leukocytes*. Hepatology, 1997. 26(5): p. 1111-4.
13. Ohira, M., et al., *Adoptive immunotherapy with liver allograft-derived lymphocytes induces anti-HCV activity after liver transplantation in humans and humanized mice*. J Clin Invest, 2009. 119(11): p. 3226-35.
14. Ohira, M., et al., *Clinical-scale isolation of interleukin-2-stimulated liver natural killer cells for treatment of liver* transplantation with hepatocellular carcinoma. Cell Transplant, 2012. 21(7): p. 1397-406.
15. Liu, D., K. F. Staveley-O'Carroll, and G. Li, *Immune-based Therapy Clinical Trials in Hepatocellular Carcinoma*. J Clin Cell Immunol, 2015. 6(6).
16. Pockros, P. J., *New direct-acting antivirals in the development for hepatitis C virus infection*. Therap Adv Gastroenterol, 2010. 3(3): p. 191-202.
17. Au, J. S. and P. J. Pockros, *Novel therapeutic approaches for hepatitis C*. Clin Pharmacol Ther, 2014. 95(1): p. 78-88.
18. Evans, M. J., C. M. Rice, and S. P. Goff, *Phosphorylation of hepatitis C virus nonstructural protein 5A modulates its protein interactions and viral RNA replication*. Proc Natl Acad Sci USA, 2004. 101(35): p. 13038-43.
19. Tellinghuisen, T. L., K. L. Foss, and J. Treadaway, *Regulation of hepatitis C virion production via phosphorylation of the NS5A protein*. PLoS Pathog, 2008. 4(3): p. e1000032.
20. Smalley, K. S., et al., *CRAF inhibition induces apoptosis in melanoma cells with non-V600E BRAF mutations*. Oncogene, 2009. 28(1): p. 85-94.
21. Zhang, Y., et al., *Screening of kinase inhibitors targeting BRAF for regulating autophagy based on kinase pathways*. Mol Med Rep, 2014. 9(1): p. 83-90.
22. Gauthier, A. and M. Ho, *Role of sorafenib in the treatment of advanced hepatocellular carcinoma: An update*. Hepatol Res, 2013. 43(2): p. 147-54.
23. Meuleman, P., et al., *Morphological and biochemical characterization of a human liver in a uPA-SCID mouse chimera*. Hepatology, 2005. 41(4): p. 847-56.
24. Stegmann, K. A., et al., *Interferon-alpha-induced TRAIL on natural killer cells is associated with control of hepatitis C virus infection*. Gastroenterology, 2010. 138(5): p. 1885-97.
25. Tu, Z., et al., *Synergy between TLR3 and IL-18 promotes IFN-gamma dependent TRAIL expression in human liver NK cells*. Cell Immunol, 2011. 271(2): p. 286-91.
26. van de Wetering, D., et al., *IL-23 modulates CD56+/CD3− NK cell and CD56+/CD3+NK-like T cell function differentially from IL-12*. Int Immunol, 2009. 21(2): p. 145-53.

The invention claimed is:

1. A method for the production of activated $CD3^-CD56^+$ NK cells comprising:
   a) isolating $CD3^-CD56^+$ NK cells from a liver perfusate; and
   b) cultivating said isolated $CD3^-CD56^+$ NK cells in the presence of IL-2, IL-15 and IFNα.

2. The method for the production of activated $CD3^-CD56^+$ NK cells according to claim 1, further comprising expanding the isolated $CD3^-CD56^+$ NK cells.

3. The method for the production of activated $CD3^-CD56^+$ NK cells according to claim 2 wherein said isolated $CD3^-CD56^+$ NK cells are expanded in the presence of irradiated cells.

4. The method according to claim 3, wherein the irradiated cells are autologous cells.

5. The method for the production of activated $CD3^-CD56^+$ NK cells according to claim 2 wherein said isolated $CD3^-CD56^+$ NK cells are expanded for from about 8 hours to about 168 hours in the presence of IL-2 and IL-15.

6. The method according to claim 1 wherein the amount of IL-2 is between 100-1000 IU/ml, the amount of IL-15 is between 20-50 ng/ml and the amount of IFNα is between 10-1000 ng/ml.

7. The method according to claim 1 wherein said isolated $CD3^-CD56^+$ NK cells are cultivated with IFNα for from about 4 hours to about 24 hours.

* * * * *